(12) United States Patent
Mahmud et al.

(10) Patent No.: US 8,101,732 B2
(45) Date of Patent: Jan. 24, 2012

(54) METHODS OF PRODUCING VALIDAMYCIN A ANALOGS AND USES THEREOF

(75) Inventors: Taifo Mahmud, Corvallis, OR (US); Zixin Deng, Shanghai (CN); Linquan Bai, Shanghai (CN); Hui Xu, Shanghai (CN); Jongtae Yang, Corvallis, OR (US)

(73) Assignee: State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 23 days.

(21) Appl. No.: 12/560,283

(22) Filed: Sep. 15, 2009

(65) Prior Publication Data
US 2010/0151528 A1 Jun. 17, 2010

Related U.S. Application Data

(60) Provisional application No. 61/097,797, filed on Sep. 17, 2008.

(51) Int. Cl.
*C07H 15/00* (2006.01)
(52) U.S. Cl. ..................................... 536/17.9
(58) Field of Classification Search .......... None
See application file for complete search history.

(56) References Cited

U.S. PATENT DOCUMENTS
5,814,616 A 9/1998 Srivastava et al.

OTHER PUBLICATIONS

Asano et al., "Microbial Degradation of Validamycin A by *Flavobacterium saccharophilum*: Enzymatic Cleavage of C—N Linkage in Validoxylamine A," *Journal of Antibiotics*, vol. 37, No. 8, pp. 859-867, 1984.
Bai et al., "Functional Analysis of the Validamycin Biosynthetic Gene Cluster and Engineered Production of Validoxylamine A," *Chemistry & Biology*, vol. 13, pp. 387-397, 2006.
Chang et al., "An Efficient Synthesis of Valienamine via Ring-Closing Metathesis," *J. Org. Chem.*, vol. 70, pp. 3299-3302, 2005.
Dong et al., "Biosynthesis of Validamycins: Identification of Intermediates in the Biosynthesis of Validamycin A by *Streptomyces hygroscopicus* var. *limoneus*," *J. Am. Chem. Soc.*, vol. 123, pp. 2733-2742, 2001.
Gust et al., "PCR-targeted *Streptomyces* gene replacement identifies a protein domain needed fo biosynthesis of the sesquiterpene soil odor geosmin," *PNAS*, vol. 100, No. 4, pp. 1541-1546, 2003.
Horii, "Valiolamine and Its *N*-Substituted Derivatives, α-$^D$-Glucosidase Inhibitors: From Validamycins to Voglibose (AO-128), an Antidiabetic Agent," *J. Takeda Res. Lab*, vol. 52, 1-26, 1993.
Kok et al., "A New Synthesis of Valienamine," *J. Org. Chem.*, vol. 66, pp. 7184-7190, 2001.
Mahmud et al., "Biosynthetic Studies on the α-Glucosidase Inhibitor Acarbose in *Actinoplanes* sp.: 2-*epi*-5-*epi*-Valiolone Is the Direct Precursor of the Valienamine Moiety," *Journal of the American Chemical Society*, vol. 30, No. 121, pp. 6973-6983, 1999.
Mahmud et al., "Synthesis of 5-*epi*-[6-$^2$H$_2$] Valiolone and Stereospecifically Monodeuterated 5-*epi*-Valiolones: Exploring the Steric Course of 5-*epi*-Valiolone Dehydratase in Validamycin A Biosynthesis," *J. Org. Chem.*, vol. 66, pp. 5066-5073, 2001.
Mahmud et al., "The Biosythesis of Acarbose and Validamycin," *The Chemical Record*, vol. 1, pp. 300-310, 2001.
Minagawa et al., "ValC, a New Type of C7-Cyclitol Kinase Involved in the biosynthesis of the Antifungal Agent Validamycin A," *ChemBioChem*, vol. 8, pp. 632-641, 2007.
Ogawa et al., "Cleavage of Validoxylamine A derivatives with *N*-Bromosuccinimide: Preparation of Blocked Synthons Useful for the Construction of Carba-oligosaccharides Composed of Imino Linkages," *J. Chem. Soc. Perkin Trans I*, pp. 3287-3290, 1991.
Ogawa et al., "Sythesis and Trehalase-inhibitory Activity of an Imino-linked Dicarba-α, α-trehalose and Analogues thereof," *J. Chem. Soc. Perkin Trans I*, pp. 691-696, 1993.
Ogawa et al., "Cleavage of the Imino Bonds of Validoxylamine A Derivatives with N-Bromosuccinimide," *Chemistry Letters*, pp. 725-728, 1989.
Shibata et al., "Inhibition of Hyphal Extension Factor Formation by Validamycin in *Rhyzoctonia solani*," *Journal of Antibiotics*, vol. 35, No. 10, pp. 1422-1423, 1982.
Shing et al., "Facile, Efficient, and Enantiospecific Syntheses of 1,1'-*N*-Linked Pseudodisaccharides as a New Class of Glycosidase Inhibitors," *J. Am. Chem. Soc.*, vol. 126, pp. 15990-15992, 2004.
Singh et al., "Genetic localization and heterologous expression of validamycin biosynthetic gene cluster isolated from *Streptomyces hygroscopicus* var. *limoneus* KCCM 11405 (IFO 12704)," *Gene*, vol. 376, pp. 13-23, 2006.
Toyokuni et al., "Biosynthetic Studies on Validamycins: A $C_2+C_2+C_3$ Pathway to an A liphatic $C_7$N Unit," *J. Am. Chem. Soc.*, vol. 109, pp. 3481-3482, 1987.
Wu et al., "A Comparative Analysis of the Sugar Phosphate Cyclase Superfamily Involved in Primary and Secondary Metabolism," *ChemBioChem*, vol. 8, pp. 239-248, 2007. Xu et al., "Genetically engineered production of 1,1'-bis-valienamine and validienamycin in *Streptomyces hygroscopicus* and their conversion to valienamine," *Applied Microbiology and Biotechnology*, vol. 81, No. 5, pp. 895-902, 2008.
Yu et al., "Gene Cluster Responsible for Validamycin Biosynthesis in *Streptomyces hygroscopicus* subsp. *jinggangensis* 5008," *ChemBioChem*, vol. 71, No. 9, pp. 5066-5076, 2005.
Zhang et al., "Biosynthesis of the $C_7$-cyclitol Moiety of Acarbose in *Actinoplanes* Species SE50/110," *J. Bio. Chem.*, vol. 277, No. 25, pp. 22853-22862, 2002.

*Primary Examiner* — Tekchand Saidha
*Assistant Examiner* — Md. Younus Meah
(74) *Attorney, Agent, or Firm* — Klarquist Sparkman, LLP

(57) ABSTRACT

This disclosure relates to validamycin A biosynthesis and in particular, to methods of producing validamycin A analogs and uses thereof. In a particular example, a method for making a validamycin A analog includes transforming a host cell with one or more recombinant DNA vectors to produce a valN-inactivated mutant; and culturing the valN-inactivated mutant in a culture medium to produce a validamycin A analog, such as 1,1'-bis-valienamine and validienamycin, and their conversion to valienamine. The present disclosure further relates to compositions including such compounds as well as methods of using the compositions, such as for antifungal agents.

3 Claims, 6 Drawing Sheets

METHODS OF PRODUCING VALIDAMYCIN A ANALOGS AND USES THEREOF

CROSS-REFERENCE TO RELATED APPLICATION

This application claims the benefit of priority under 35 U.S.C. §119(e) to U.S. Provisional Application No. 61/097,797 filed on Sep. 17, 2008, which is incorporated herein by reference in its entirety.

ACKNOWLEDGMENT OF GOVERNMENT SUPPORT

This invention was made with government support under R01 AI-61528 awarded by the National Institutes of Health. The United States Government has certain rights in the invention.

FIELD

This disclosure relates to validamycin A biosynthesis and in particular, to methods of producing validamycin A analogs and uses thereof.

BACKGROUND

The antifungal antibiotic validamycin A is a commercially of interest compound due to its wide application in controlling fungal infections of rice plants caused by *Rhizoctonia solani* (also referred to as *Pellicularia sasakii*) (Shibata et al., *J. Antibiot. (Tokyo)* 35:1422-1423, 1982). Structurally, validamycin A includes an unsaturated aminocyclitol unit valienamine, the saturated aminocyclitol unit validamine and glucose. The valienamine moiety is believed to be the pharmacophore of this compound and is also present in a number of other important aminocyclitols, such as the α-glucosidase inhibitors acarbose, the adiposins, the amylostatins, and the trestatins. In addition, the valienamine unit is a synthetic precursor of the clinically used antidiabetic agent voglibose (Horii, *J. Takeda Res. Lab.* 52: 1-26, 1993).

Due to its high commercial value, efforts have been made by many groups to obtain valienamine by chemical synthesis. During the past twenty years more than a dozen enantiospecific syntheses have been described for valienamine, however, its commercial supply still relies on natural product degradation processes (Asano et al., *J. Antibiot. (Tokyo)* 37: 859-867, 1984).

As part of efforts to use biosynthetic approaches to generate novel aminocyclitol analogs, the biosynthetic gene cluster of validamycin A was identified in *S. hygroscopicus* subsp. *jinggangensis* 5008 (Bai et al., *Chem. Biol.* 13: 387-397, 2006). Sequencing of the 45 kb DNA fragment containing the gene cluster revealed 16 structural genes, two regulatory genes, five genes related to transport, transposition/integration, tellurium resistance, and another four genes with no identity. Among those believed to be involved in the synthesis of validamycin A in *S. hygroscopicus* 5008 are the 2-epi-5-epi-valiolone synthase (ValA), the nucleotidyltransferase (ValB), the cyclitol kinase (ValC), the cyclitol epimerase (ValD), the glycosyltransferase (ValG), the putative dehydratase (ValK), the validoxylamine A 7'-phosphate synthase (ValL), the aminotransferase (ValM), and the cyclitol reductase (ValN).

SUMMARY

This disclosure describes validamycin analogs, including validienamycin, and their manufacture. In one embodiment, the analogs are produced by mutant strains of *Streptomyces* organisms, such as *Streptomyces hygroscopicus*. Methods for making a validamycin A analog include transforming a host cell with one or more recombinant DNA vectors to produce a valN-inactivated mutant and culturing the valN-inactivated mutant in a culture medium to produce a compound of the formula

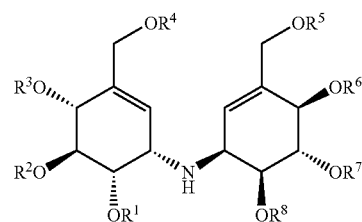

wherein $R^1$-$R^8$ independently are selected from H, acyl, carbohydrate, lower alkyl, amino acid, fatty acid, and protecting groups. In some embodiments, the compound has the formula

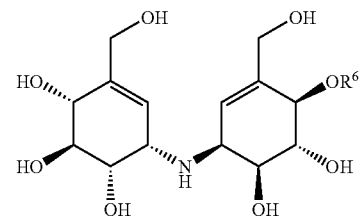

wherein $R^6$ is selected from acyl, lower alkyl, carbohydrate, amino acid, or protecting groups. In one specific example, $R^6$ is a carbohydrate, such as a hexose. In further embodiments, the method produces a compound having the formula

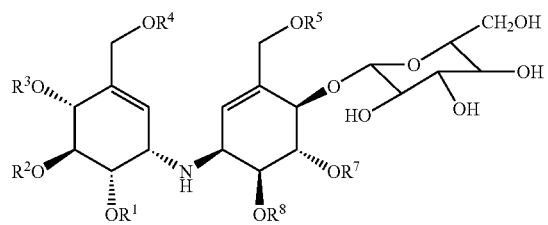

In further examples, the method produces a compound with one of the following formulas:

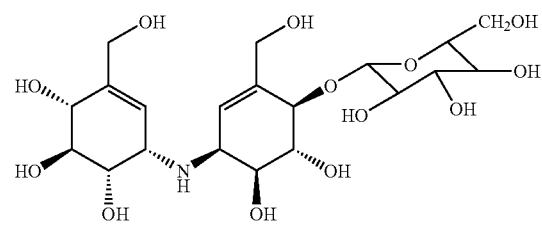

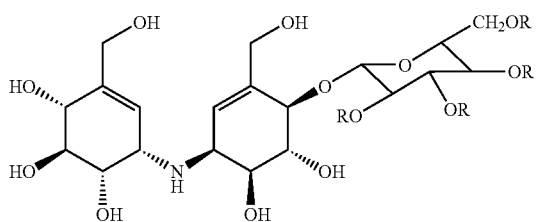

wherein R can be an acetyl or benzyl groups, or

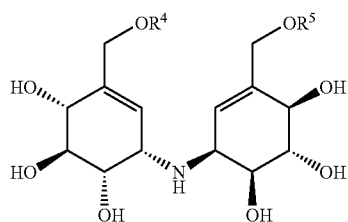

wherein $R^4$ and $R^5$ can be acyl or lower alkyl groups.

Also disclosed are validamycin analogs with the following chemical structures:

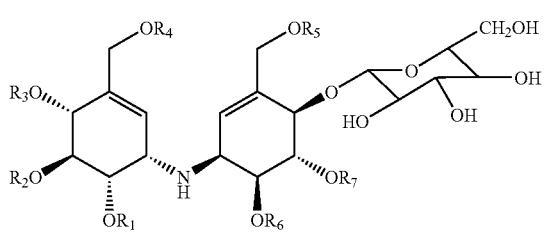

wherein $R_1$-$R_7$ independently are selected from H, acyl, carbohydrate, lower alkyl, amino acid, fatty acid, and protecting groups. In certain examples, a validamycin analog has the chemical structure of

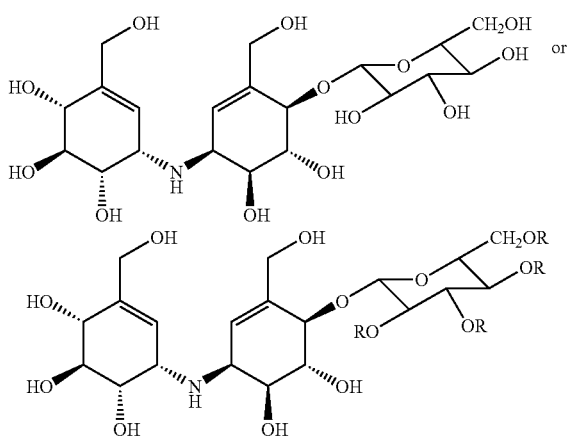

wherein R is an acetyl or benzyl group.

The foregoing and other features of the disclosure will become more apparent from the following detailed description, which proceeds with reference to the accompanying figures.

SEQUENCE LISTING

The nucleic and amino acid sequences listed in the accompanying sequence listing are shown using standard letter abbreviations for nucleotide bases, and three letter code for amino acids, as defined in 37 C.F.R. §1.822. Only one strand of the nucleic acid sequence is shown, but the complementary strand is understood as included by any reference to the displayed strand. In the accompanying sequence listing:

SEQ ID NOs: 1-4: are oligonucleotide sequences employed to amplify a disclosed valN mutant.

SEQ ID NO: 5 is the nucleic acid sequence for a disclosed valN mutant.

DETAILED DESCRIPTION

I. Introduction

One of the essential genes for validamycin A biosynthesis is valN, which encodes a protein homologous with the zinc-dependent sorbitol dehydrogenase from *Geobacillus thermodenitrificans* NG80-2 (28% identity, 45% similarity) and the alcohol dehydrogenase from *Prosthecochloris vibrioformis* DSM 265 (29% identity, 42% similarity). Both sorbitol and alcohol dehydrogenases are $NAD^+$-dependent enzymes that catalyze the oxidation of an alcohol to a ketone. ValN also shares conserved domains with other dehydrogenase proteins, such as the shikimate 5-dehydrogenases and the ketopantoate reductases, which catalyze the conversions of shikimate to 5-dehydroshikimate and (R)-pantoate to 2-dehydropantoate, respectively. Therefore, it was postulated that ValN would catalyze the reduction of the C-1 ketone of one of the early intermediates in the validamycin pathway to its corresponding alcohol and thus inactivation of the cyclitol reductase (valN) gene in the validamycin producer would abolish the production of validamycin A.

Figure 2:
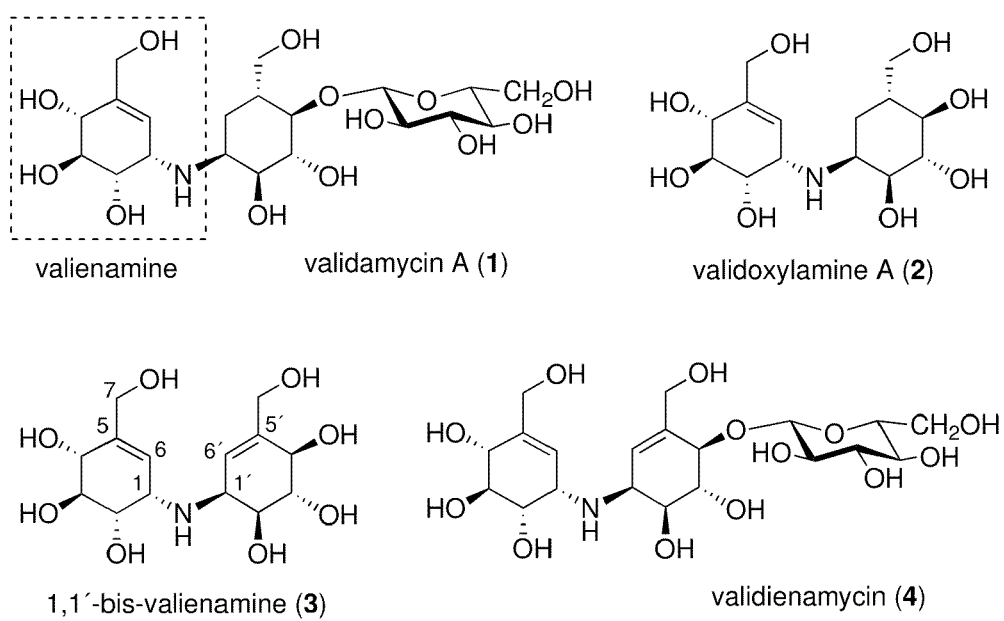
FIG. 2 illustrates the chemical structures of validamycin A and exemplary validamycin A analogs.

To investigate the function of valN in validamycin A biosynthesis, the valN gene in *S. hygroscopicus* 5008 was inactivated and the metabolite profile of the mutant strain was analyzed. While the inventors discovered that the mutant strain lacked the ability to produce validamycin A, surprisingly, the mutant strain produced two unsaturated analogs, 1,1'-bis-valienamine and validienamycin (FIG. 2). These findings indicate that ValN is responsible for the reduction of the C-5/C-6 double bond, rather than the C-1 ketone.

Herein is disclosed the construction of a representative valN mutant strain, isolation and structure elucidation of the new metabolites produced by such strain, the antifungal activity of the new metabolites, and methods of their efficient conversion to valienamine. In one embodiment, a valN-inactivated mutant cell has an amino acid sequence with at least 95% sequence identity to SEQ ID NO: 6. In other embodiments, a valN-inactivated mutant cell has an amino acid sequence as set forth in SEQ ID NO: 6. In an embodiment, the valN-inactivated mutant cell has a nucleic acid sequence with at least 95% sequence identity to SEQ ID NO: 5. In a particular embodiment, the nucleic acid sequence of the valN-inactivated mutant cell is as set forth in SEQ ID NO: 5.

Also disclosed herein is a recombinant DNA vector including a valN-inactivated mutant. A host cell transformed with one or more recombinant DNA vectors is also provided herein. In a particular embodiment, the host cell is a *Streptomyces* cell.

In one embodiment, a method for making a validamycin A analog is disclosed that includes transforming a host cell with one or more recombinant DNA vectors to produce a valN-inactivated mutant cell and culturing the valN-inactivated mutant cell in a culture medium to produce a compound of the formula

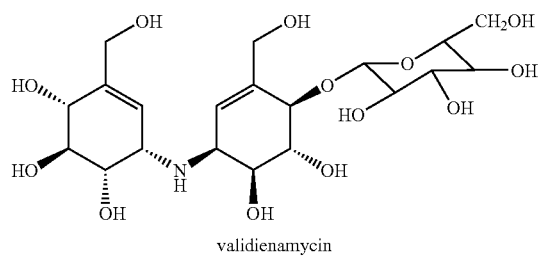

validienamycin and a compound of the formula

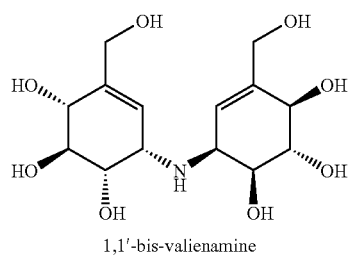

1,1'-bis-valienamine

In some embodiments, the method includes treating the 1,1'-bis-valienamine with N-bromosuccinimide (NBS).

Optionally, the method also includes purifying the resulting product of the 1,1'-bis-valienamine with NBS, such as by ion exchange column chromatography, thereby producing substantially pure valienamine. In certain embodiments, the method further includes converting the substantially pure valienamine to voglibose.

In one specific embodiment, a method for making a validamycin A analog, includes transforming a host cell with one or more recombinant DNA vectors to produce a valN-inactivated mutant; and culturing the valN-inactivated mutant in a culture medium to produce a compound of the formula

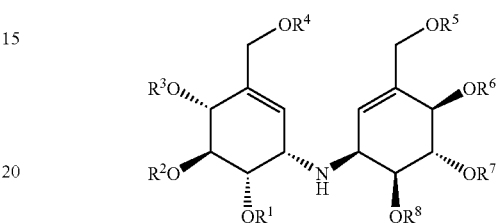

wherein $R^1$-$R^8$ independently are selected from H, acyl, carbohydrate, lower alkyl, amino acid, fatty acid, and protecting groups. In some embodiments, the compound has the formula

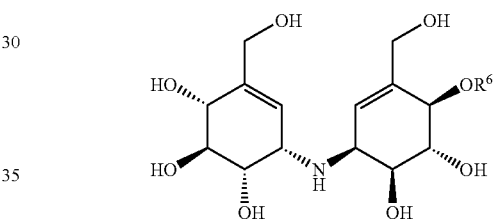

wherein $R^6$ is selected from acyl, lower alkyl, carbohydrate, amino acid, or protecting groups. In one specific example, $R^6$ is a carbohydrate, such as a hexose. In further embodiments, the method produces a compound having the formula

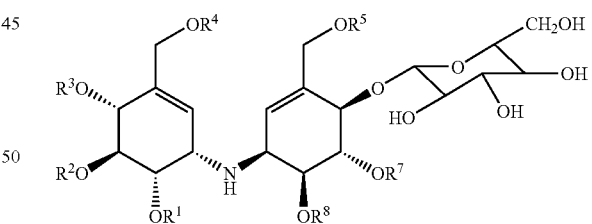

In further examples, the method produces a compound with one of the following formulas:

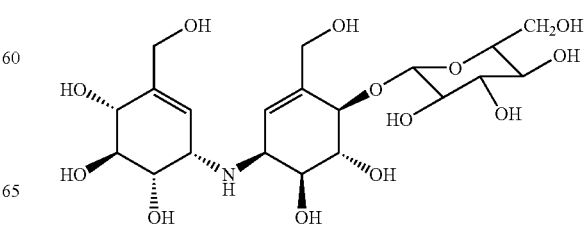

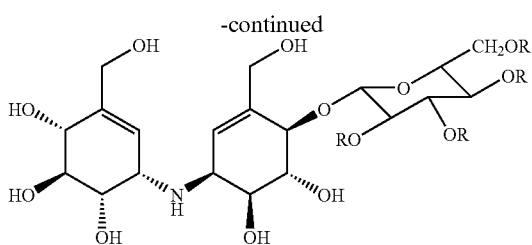

wherein R can be an acetyl or benzyl groups, or

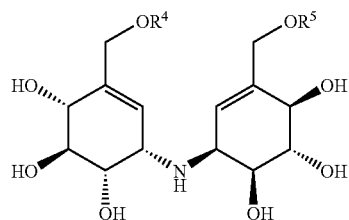

wherein $R^4$ and $R^5$ can be acyl or lower alkyl groups.

In additional embodiments, validamycin A analogs with the following formula are disclosed:

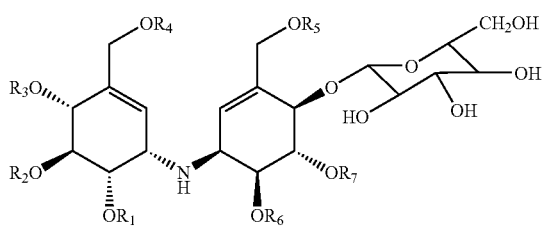

wherein $R_1$-$R_7$ independently are selected from H, acyl, carbohydrate, lower alkyl, amino acid, fatty acid, and protecting groups is disclosed. In one embodiment, the compound has one of the following structures:

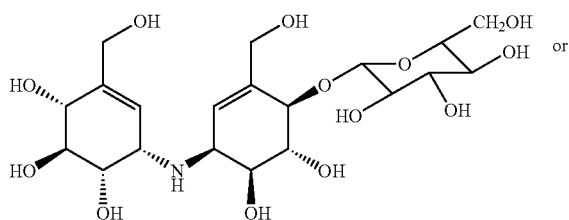

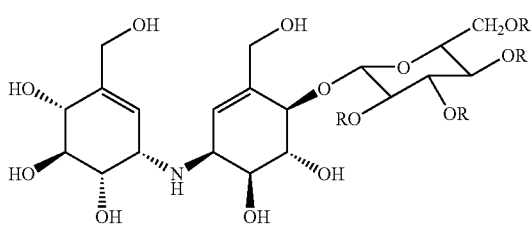

wherein R is an acetyl or benzyl group.

II. Abbreviations and Terms a. Abbreviations

| MS: | mass spectrometry |
|---|---|
| NBS: | N-bromosuccinimide |
| NMR: | nuclear magnetic resonance |
| ORF: | open reading frame |
| PCR: | polymerase chain reaction |
| TLC: | thin layer chromatography |
| YMG: | yeast extract, malt extract and glucose | b. Terms

Unless otherwise noted, technical terms are used according to conventional usage. Definitions of common terms in molecular biology may be found in Benjamin Lewin Genes V published by Oxford University Press, 1994 (ISBN 0-19-854287-9); Kendrew et al. (eds.) *The Encyclopedia of Molecular Biology*, published by Blackwell Science Ltd., 1994 (ISBN 0-632-02182-9); and Robert A. Meyers (ed.) *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Acyl: A group of the formula RC(O)— wherein R is an organic group.

Aliphatic: Moieties including alkyl, alkenyl, alkynyl, halogenated alkyl and cycloalkyl groups as described below. A "lower aliphatic" group is a branched or unbranched aliphatic group having from 1 to 10 carbon atoms.

Alkyl: A branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. The terms "halogenated alkyl" or "haloalkyl group" refer to an alkyl group as defined above with one or more hydrogen atoms present on these groups substituted with a halogen (F, Cl, Br, I). The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous. Optionally substituted groups, such as "substituted alkyl," describes groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

Alkenyl: A hydrocarbon group of 2 to 24 carbon atoms and structural formula containing at least one carbon-carbon double bond.

Alkynyl: A hydrocarbon group of 2 to 24 carbon atoms and a structural formula containing at least one carbon-carbon triple bond.

Allelic variant: A naturally occurring alternate form of a polypeptide that is characterized as having a substitution, deletion, or addition of one or more amino acids as compared to the wildtype form of the sequence. In one example, the variant does not alter the biological function of the polypeptide. In other examples, the variant includes a mutation that alters the biological function of the polypeptide.

Amino acid: Amino acid refers to both natural and unnatural amino acids, including their D and L stereoisomers for chiral amino acids. Natural and unnatural amino acids are well known to those of ordinary skill in the art. Common natural amino acids include, without limitation, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Uncommon and unnatural amino acids include, without limitation, allyl glycine (AllylGly), biphenylalanine (Bip), citrulline (Cit), 4-guanidinophenylalanine (Phe(Gu)), homoarginine (hArg), homolysine (hLys), 2-napthylalanine (2-Nal), ornithine (Orn) and pentafluorophenylalanine (F5Phe).

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation, aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan and tyrosine are classified as both polar and aromatic amino acids. Additional amino acids that are classified in each of the above groups are known to those of ordinary skill in the art. Exemplary validamycin analogs disclosed herein are functionalized, chemically or biosynthetically, with one or more amino acid residues.

Amplification: When used in reference to nucleic acids, amplification refers to techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a molecule derived from the base structure. A mimetic is a molecule that mimics the activity of another molecule, such as a biologically active molecule. Biologically active molecules can include chemical structures that mimic the biological activities of a compound.

Antibiotic: A substance that can destroy or inhibit the growth of other microorganisms. Antibiotics are often produced by or derived from certain fungi, bacteria, and other organisms. For example, validamycin is an antibiotic.

Culturing: The process by which either prokaryotic or eukaryotic cells are grown under controlled conditions. Culture conditions vary widely for each cell type, and variation of conditions for a particular cell type can result in different phenotypes being expressed. Aside from temperature and gas mixture, the most commonly varied factor in culture systems is the growth medium. Recipes for growth media can vary in pH, glucose concentration, growth factors, and the presence of other nutrient components. As used herein, culturing refers to the growing of prokaryotic cells, such as *E. coli* cells or *Streptomyces* cells (such as genetically engineered *Streptomyces hygroscopicus* cells), transfected with the disclosed valN mutant under conditions that allow the production of validamycin analogs.

Conservative substitution: Amino acid substitutions that do not substantially alter the activity (specificity or binding affinity) of the molecule. Typically conservative amino acid substitutions involve substitutions of one amino acid for another amino acid with similar chemical properties (e.g., charge or hydrophobicity). The following table shows exemplar conservative amino acid substitutions:

| Original Residue | Conservative Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |

-continued

| Original Residue | Conservative Substitutions |
|---|---|
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

DNA (deoxyribonucleic acid): A long chain polymer which comprises the genetic material of most living organisms (some viruses have genes comprising ribonucleic acid (RNA). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Domain: A portion of a molecule such as proteins or nucleic acids that is structurally and/or functionally distinct from another portion of the molecule.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Functional fragments and variants of a polypeptide: Included are those fragments and variants that maintain one or more functions of the parent polypeptide. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential function(s) of a protein. See Stryer *Biochemistry* 3rd Ed., (c) 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al., *J. Immunol.* 159(5): 2502-12, 1997). Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionuclides, and various enzymatic modifications, as will be readily appreciated by those well skilled in the art. Many methods for labeling polypeptides and labels useful for such purposes are well known in the art, and include radioactive isotopes such as $^{32}P$, ligands which bind to or are bound by labeled specific binding partners (e.g., antibodies), fluorophores, chemiluminescent agents, enzymes, and antiligands. Functional fragments and variants can be of varying length. For example, some fragments have at least 10, 25, 50, 75, 100, 200, or even more amino acid residues.

Gene Cluster: A set of genetic elements grouped together on the chromosome, the protein products of which have a related function, such as forming a natural product biosynthetic pathway. A validamycin biosynthetic gene cluster from *S. hygroscopicus* subsp. *jinggangensis* 5008 can be formed by the gene cluster including 16 structural genes, two regulatory genes, five genes related to transport, transposition/integration, tellurium resistance, and another four genes with no obvious identity. In one example, a validamycin A gene cluster has a nucleic acid sequence as set forth in GenBank Accession No. DQ164098, which is incorporated by reference in its entirety as of Sep. 17, 2008.

Heterologous: As it relates to nucleic acid sequences such as coding sequences and control sequences, "heterologous" denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different than the native gene). Similarly, a host cell transformed with a construct which is not normally present in the host cell would be considered heterologous for purposes of this disclosure.

Homologous amino acid sequence: Any polypeptide which is encoded, in whole or in part, by a nucleic acid sequence that hybridizes to any portion of the coding region nucleic acid sequences. A homologous amino acid sequence is one that differs from an amino acid sequence shown in the sequence listing by one or more conservative amino acid substitutions. Such a sequence also encompasses allelic variants (defined above) as well as sequences containing deletions or insertions which retain the functional characteristics of the polypeptide. Preferably, such a sequence is at least 75%, more preferably 80%, more preferably 85%, more preferably 90%, more preferably 95%, and most preferably 98% identical to any one of the amino acid sequences.

Homologous amino acid sequences include sequences that are identical or substantially identical to the amino acid sequences of the sequence listing. By "substantially identical to the amino acid sequence" it is meant a sequence that is at least 90%, preferably 95%, more preferably 97%, and most preferably 99% identical to an amino acid sequence of reference. In an example, the sequence is at least 90% identical to the referenced amino acid sequence and differs from the sequence of reference by conservative amino acid substitutions. Polypeptides having a sequence homologous to any one of the amino acid sequences of the sequence listing include naturally-occurring allelic variants, as well as mutants or any other non-naturally occurring variants that retain the inherent characteristics (e.g., biosynthetic activity) of any polypeptide of the sequence listing. Homology can be measured using sequence analysis software such as Sequence Analysis Software Package of the Genetics Computer Group, University of Wisconsin Biotechnology Center, 1710 University Avenue, Madison, Wis. 53705. Amino acid sequences can be aligned to maximize identity. Gaps can also be artificially introduced into the sequence to attain optimal alignment. Once the optimal alignment has been set up, the degree of homology is established by recording all of the positions in which the amino acids of both sequences are identical, relative to the total number of positions. Homologous polynucleotide sequences are defined in a similar way. Preferably, a homologous sequence is one that is at least 45%, 50%, 60%, 70%, 75%, 80%, 85%, 86%, 87%, 88%, 89%, 90%, 91%, 92%, 93%, 94%, 95%, 96%, 97%, 98%, 99% or identical to any one of the coding sequences.

Inactivated valN: A condition which results in a non-functional valN gene. Inactivation can be accomplished by insertion of one or more nucleotides to the valN nucleic acid sequence, replacement of one or more nucleotides, deletion of one or more nucleotides or any other mechanism that results in a non-functional valN gene.

Inhibit: To decrease, limit or block the action or function of a molecule. In an example, the activation of valN is decreased, limited or blocked by a valN inhibitory molecule.

Isolated: An isolated biological component (such as a nucleic acid molecule or protein) is one that has been substantially separated or purified away from other biological components in the cell of the organism in which the component naturally occurs, such as other chromosomal and extra-chromosomal DNA and RNA, proteins and organelles. With respect to nucleic acids and/or polypeptides, the term can refer to nucleic acids or polypeptides that are no longer flanked by the sequences typically flanking them in nature. Nucleic acids and proteins that have been isolated include nucleic acids and proteins purified by standard purification methods. The term also embraces nucleic acids and proteins prepared by recombinant expression in a host cell as well as chemically synthesized nucleic acids.

Nucleic Acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15, or 20 bases.

Open reading frame (ORF): A series of nucleotide triplets (codons) coding for amino acids without any internal termination codons. These sequences are usually translatable into a peptide. For example, ORF, open reading frame, and validamycin ORF refer to an open reading frame in the validamycin biosynthetic gene cluster as isolated from *Streptomyces hygroscopicus*. The term also embraces the same ORFs as present in other validamycin-synthesizing organisms. The term encompasses allelic variants and single nucleotide polymorphisms (SNPs). In certain instances the term validamycin ORF is used synonymously with the polypeptide encoded by the validamycin ORF and may include conservative substitutions in that polypeptide. The particular usage will be clear from context.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Probes and primers: Nucleic acid probes and primers can be readily prepared based on the nucleic acid molecules provided in this disclosure. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992).

Primers are short nucleic acid molecules, preferably DNA oligonucleotides, 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (In *Current Protocols in Molecular Biology*, Greene Publ. Assoc. and Wiley-Intersciences, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 17, 20, 23, 25, 30, 35, 40, 45, 50 or more consecutive nucleotides of desired nucleotide sequence. In particular examples, probes or primers can be at least 100, 250, 500, 600 or 1000 consecutive nucleic acids of a desired nucleotide sequence.

Protein: A biological molecule expressed by a gene and comprised of amino acids.

Purified or substantially purified: The term purified does not require absolute purity; rather, it is intended as a relative term. Thus, for example, a compound is one in which the compound referred to is more pure than the other compounds or contaminants within the mixture. Substantially pure or substantially purified refers to a condition in which the mixture contains at least 80% of the compound referred to, such as at least 85%, at least 90%, at least 95%, at least 98%, including 81%, 82%, 83%, 84%, 85%, 86%, 87%, 88%, 89%, 90%, 91%, 92%, 93%, 94%, 95%, 96%, 97%, 98%, 99% or 100%.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. "Recombinant" also is used to describe nucleic acid molecules that have been artificially manipulated, but contain the same control sequences and coding regions that are found in the organism from which the gene was isolated.

*Rhizoctonia solani*: A basidiomycete fungus which primarily attacks below ground plant parts such as the seeds, hypocotyls, and roots, but is also capable of infecting above ground plant parts (e.g., seeds, pods, fruits, leaves and stems). The most common symptom of *Rhizoctonia* disease is referred to as "damping-off" characterized by non-germination of severely infected seed whereas infected seedlings can be killed either before or after they emerge from the soil. Infected seedlings not killed by the fungus often have cankers, which are reddish-brown lesions on stems and roots.

*Sclerotinia sclerotiorum*: A fungus that is capable of infecting numerous crops including lettuce, broccoli, cabbage, cauliflower, carrots, celery, beans, tomato, peppers, potatoes, stocks, sunflower, eggplant, squash, artichoke, asparagus, beet, broad bean, flower crops and landscape shrubs. A typical initial symptom of *S. sclerotiorum* infection is the presence of a cottony, white, dense mat of mycelial growth (mass of fungus strands) on the surface of the host and on the adjacent soil surface. Within this fluffy white mass, dense white bodies of fungus form. These bodies become black and hard as they mature and are called sclerotia. The sclerotia function like seeds and allow the fungus to survive for several years in the soil.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., *FEMS Microbiol. Lett.,* 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al., *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins (or nucleic acids) with even greater similarity to the reference sequences will show increasing percentage identities when assessed by this method, such as at least 50%, at least 60%, at least 70%, at least 80%, at least 85%, at least 90%, or at least 95% sequence identity.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, or at least 98% sequence identity.

An alternative indication that two nucleic acid molecules are closely related is that the two molecules hybridize to each other.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

*Streptomyces*: A genus of Actinobacteria, a group of Gram-positive and generally high GC-content bacteria. Streptomycetes are found predominantly in soil and in decaying vegetation, and most produce spores. They are characterized by a complex secondary metabolism and produce a large number of antibiotics that are in clinical use (such as, neomycin and chloramphenicol).

Transforming or Transfecting: A process by which a nucleic acid molecule is introduced into cell, for instance by molecular biology techniques, resulting in a transfected (or transformed) cell. As used herein, the term transformation or transfection encompasses all techniques by which a nucleic acid molecule might be introduced into such a cell, including transduction with viral vectors, transfection with plasmid vectors, and introduction of DNA by electroporation, lipofection, and particle gun acceleration.

Validamycin A: An antifungal agent the can be used as a crop protectant and the source of valienamine, the precursor of the antidiabetic drug voglibose. The structure of validamycin A is

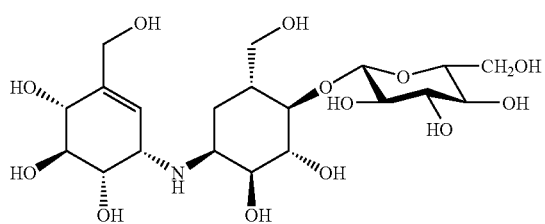

valN gene: One of the genes involved in validamycin A biosynthesis, which encodes a cyclitol reductase protein homologous with the zinc-dependent sorbitol dehydrogenase from *Geobacillus thermodenitrificans* NG80-2 (28% identity, 45% similarity) and the alcohol dehydrogenase from *Prosthecochloris vibrioformis* DSM 265 (29% identity, 42% similarity). A ValN protein also shares conserved domains with other dehydrogenase proteins, such as the shikimate 5-dehydrogenases and the ketopantoate reductases, which catalyze the conversions of shikimate to 5-dehydroshikimate and (R)-pantoate to 2-dehydropantoate, respectively.

Vector: A nucleic acid molecule that can be introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In case of conflict, the present specification, including explanations of terms, will control. In addition, the materials, methods, and examples are illustrative only and not intended to be limiting.

Suitable methods and materials for the practice of the disclosed embodiments are described below. In addition, any appropriate method or technique well known to the ordinarily skilled artisan can be used in the performance of the disclosed embodiments. Some conventional methods and techniques applicable to the present disclosure are described, for example, in Sambrook et al., *Molecular Cloning: A Laboratory Manual*, $2^{nd}$ ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

All publications, patent applications, patents, and other references mentioned herein are incorporated by reference in their entirety. In case of conflict, the present specification, including explanations of terms, will control.

III. Biosynthetic Production of Validamycin Analogs

Biosynthetic methods are disclosed herein for synthesizing validamycin analogs. In certain embodiments, the biosynthetic methods employ variant enzymes that alter the biosynthesis, for example to improve efficiency or produce analog compounds. As disclosed herein, cloning and expression of at least one open reading frame (ORF) of a validamycin A biosynthetic gene cluster in a heterologous host, such as *E. coli* or *Streptomyces*, can be used to increase production of validamycin A, a validamycin A precursor, a validamycin A intermediate, or an enzyme or protein included within the gene cluster. In addition, genetic recombination and domain-exchange constructs permit the creation of validamycin structures that would be difficult to make using traditional synthetic methodologies. For example, 1,1'-bis-valienamine is a very complex compound with a densely functionalized structure, which makes it very difficult to be synthesized chemically. Thus, alternative methods of structure modification are needed.

In an embodiment, a recombinant expression system is selected from prokaryotic hosts. Bacterial cells are available from numerous sources, including commercial sources known to those skilled in the art, such as the American Type Culture Collection (ATCC; Manassas, Va.). Commercial sources of cells used for recombinant protein expression also provide instructions for usage of such cells.

One representative heterologous host system for expression of a validamycin A gene cluster is *Streptomyces* sp. *Streptomyces* spp. are useful heterologous host systems because they are easily grown, plasmids and cosmids for the expression and/or integration of biosynthetic gene clusters are well characterized, and they house many of the modifying and auxiliary enzymes required to produce functional pathways (Donadio et al., *J. Biotechnol.*, 99:187-198, 2002).

Another representative heterologous host system for expression of a validamycin A gene cluster (or one or more of its ORFs) is *E. coli*. *E. coli* is an attractive artificial expression system because it is fast growing and easy to genetically manipulate. Recent advances in *E. coli*-based expression systems have greatly aided efforts to simultaneously express multiple genes in a single host organism. Multiple ORFs from a complex biosynthetic system (such as ORFs from a validamycin gene cluster including, but not limited to one or more ORFs involved in the synthesis of validamycin A) can now be expressed simultaneously in *E. coli*. To ensure adequate and coordinate production of multiple biosynthetic enzymes from a single pathway, each ORF is optionally placed under control of a single type of promoter, such as the inducible T7 promoter. Novagen (San Diego, Calif.) has introduced the Duet™ vectors, which are designed with compatible replicons and drug resistance genes for effective propagation and maintenance of four plasmids in a single *E. coli* cell. This allows for the co-expression of up to eight proteins.

The activity of particular enzymes may require the correct post-translational modification of the corresponding peptidyl carrier protein. Typically, this is accomplished by the co-expression of an appropriate phosphopantetheinyl transferase (PPtase) gene, for example sfp from *Bacillus subtilus* (Quadri et al., *Biochem.*, 37(6):1585-1595, 1998).

The choice of the expression system is influenced by the features desired for the expressed polypeptides. Any transducible cloning vector can be used as a cloning vector for the nucleic acid constructs presently disclosed. If large clusters are to be expressed, it is preferable that phagemids, cosmids, P is, YACs, BACs, PACs, HACs, MACs, or similar cloning vectors are used for cloning the nucleotide sequences into the host cell and subsequent expression. These vectors are advantageous due to their ability to insert and stably propagate larger fragments of DNA, compared to M13 phage and lambda phage.

In an embodiment, one or more of the ORFs or variant thereof of the validamycin A gene cluster can be inserted into one or more recombinant DNA vectors, using methods known to those of skill in the art. In one example, one or more of the ORFs or variant thereof of the validamycin A gene cluster (as identified in S. hygroscopicus subsp. jinggangensis 5008 by Bai et al., Chem. Biol. 13: 387-397, 2006; this reference is hereby incorporated by reference in its entirety) involved in the synthesis of validamycin A, such as an ORF encoding 2-epi-5-epi-valiolone synthase (ValA), the nucleotidyltransferase (ValB), the cyclitol kinase (ValC), the cyclitol epimerase (ValD), the glycosyltransferase (ValG), the putative dehydratase (ValK), the validoxylamine A 7'-phosphate synthase (ValL), the aminotransferase (ValM), or the cyclitol reductase (ValN) can be inserted into one or more recombinant DNA vectors. Vectors are used to introduce validamycin A biosynthesis genes or a gene cluster into host cells either integrated or episomal. Prokaryotic host cells or other host cells with rigid cell walls may be transformed using any method known in the art, including, for example, calcium phosphate precipitation, or electroporation. Representative prokaryote transformation techniques are described in Dower (*Genetic Engineering, Principles and Methods*, 12: 275-296, Plenum Publishing Corp., 1990) and Hanahan et al. (*Methods Enzymol.*, 204: 63, 1991). Vectors include one or more expression control sequences operably linked to the desired ORF(s). Typically, the expression cassette includes a promoter that is functional in the selected host system and can be constitutive or inducible. In an embodiment, the expression cassette includes for each ORF a promoter, ribosome binding site, a start codon (ATG) if necessary, and optionally a region encoding a leader peptide in addition to the desired DNA molecule and stop codon. In addition, a 3' terminal region (translation and/or transcription terminator) can be included within the cassette. The ORF constituted in the DNA molecule may be solely controlled by the promoter so that transcription and translation occur in the host cell. Promoter encoding regions are well known and available to those of skill in the art. Examples of promoters include control sequences derived from validamycin gene clusters, bacterial promoters (such as those derived from sugar metabolizing enzymes, such as galactose, lactose and maltose), promoter sequences derived from biosynthetic enzymes such as tryptophan, the beta-lactamase promoter system, bacteriophage lambda PL and TF and viral promoters.

The presence of additional regulatory sequences within the expression cassette may be desirable to allow for regulation of expression of the one or more ORFs relative to the growth of the host cell. These regulatory sequences are well known in the art. Examples of regulatory sequences include sequences that turn gene expression on or off in response to chemical or physical stimulus as well as enhancer sequences. In addition, to the regulatory sequences, selectable markers can be included to assist in selection of transformed cells. For example, genes that confer antibiotic resistance or sensitivity to the plasmid may be used as selectable markers.

It is contemplated that various validamycin A ORFs and/or gene cluster or proteins of interest can be cloned into one or more recombinant vectors as individual cassettes, with separate control elements, or under the control of a single control element (e.g., a promoter). In an embodiment, the cassettes include two or more restriction sites to allow for the easy deletion and insertion of other open reading frames so that hybrid synthetic pathways can be generated. The design and use of such restriction sites is well known in the art and can be carried out by using techniques described above such as PCR or site-directed mutagenesis. Proteins expressed by the transformed cells can be recovered according to standard methods well known to those of skill in the art. For example, proteins can be expressed with a convenient tag to facilitate isolation. Further, the resulting polypeptide can be purified by affinity chromatography by using a ligand (such as a compound related to validamycin A) that binds to the polypeptide.

The resulting validamycin A mutant/variant strains may be used in the methods of the present disclosure to produce biologically active compounds. Representative methods include cultivating and recovering the cells or a biological agent from the culture medium. It may be desirable thereafter to form the free acid or a salt or ester by methods known by one of ordinary skill in the art.

In an example, a validamycin A mutant or variant strain is cultivated in a nutrient medium suitable for production of the biological substance using methods known in the art. For example, the cell may be cultivated by shake flask cultivation, small-scale or large-scale fermentation (including continuous, batch, fed-batch, or solid state fermentations) in laboratory or industrial fermentors in a suitable medium and under conditions allowing the biological substance to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection).

In one example, the nutrient media for the cultivation of the validamycin A mutant or variant strain contains, in the range of about 0.1 to about 10%, a complex organic nitrogen source such as yeast extract, corn steep liquor, vegetable protein, seed protein, hydrolysates of such proteins, milk protein hydrolysates, fish or meat extracts, or hydrolysates such as peptones. In an alternative example, chemically defined sources of nitrogen can be used such as urea, amides, single or mixtures of amino acids such as valine, asparagine, glutamic acid, proline, and phenylalanine. In further examples, carbohydrates (0.1-5%) are included in the nutrient media; starch or starch hydrolysates such as dextrin, sucrose, lactose or other sugars or glycerol or glycerol esters may also be used. The source of carbon can be derived from vegetable oils or animal fats. Carboxylic acids and their salts can be included as a source of carbon for growth. A particularly suitable low cost medium is one containing soy bean flour plus dried malt distillers' solubles plus dextrin.

In an example, mineral salts such NaCl, KCl, $MgCl_2$, $ZnCl_2$, $FeCl_3$, $Na_2SO_4$, $FeSO_4$, $MgSO_4$ and $Na^+$ or $K^+$ salts of phosphoric acid are added to the media described above particularly if chemically defined. In further examples, $CaCO_3$ (as a source of $Ca^{++}$ ions or for its buffering action), salts of trace elements (such as nickel, cobalt or manganese) or vitamins are added to the media.

After production, the biological substances can be purified and/or analyzed by methods well known to one of skill in the art including a multitude of chromatographic and spectroscopic techniques, including HPLC, LC-MS, GC-MS, and NMR analysis.

In certain embodiments, the substances produced as described herein will be isolated from mutant *S. hygroscopicus* strains or other host organisms and will provide validamycin analogs for biochemical evaluation or further semisynthetic modification. For example, a compound produced using a variant validamycin A strain can be isolated and semisynthetically modified by one or more chemical reactions to produce yet identified validamycin analogs.

In one example, a variant strain of *Streptomyces*, such as *Streptomyces hygroscopicus*, can be produced in which one or more of the structural genes involved in the production of validamycin A is inactivated or inhibited. For example, a strain of *Streptomyces hygroscopicus* can be produced in which the valN gene is inactivated or inhibited by methods known to those of skill in the art.

In a particular embodiment, a valN-inactivated mutant strain of *Streptomyces hygroscopicus* subsp. *jinggangensis* 5008 is prepared by using ReDirect Technology (Gust et al., Proc. Natl. Acad. Sci. USA 100: 1541-1546, 2003). For example, a 1449-bp replacement fragment is obtained by amplifying the aac(3)IV-oriT cassette from pIJ773 using primers specific for ValN (e.g., primers with sequences corresponding to SEQ ID NOS: 1 and 2). A 7096-bp BamHI fragment from cosmid 17F2 containing valN is cloned into BamHI digested pHZ1358, to generate pJTU751. Plasmid pJTU751 can then be transferred into *E. coli* BW25113 harboring the λRED plasmid pIJ790. ValN in pJTU751 can be replaced by the above PCR product to generate plasmid pJTU753, which has 3924-bp upstream and 2244-bp downstream sequences flanking the valN gene for double-crossover recombination and transformed into *S. hygroscopicus* 5008 by conjugation. Replacement of valN in the resulting XH-2 mutant can then be confirmed by PCR amplification with the primers of ValN-det-F (5'-TGCTTCCGCTGCTTC-TAC-3'; SEQ ID NO: 3) and ValN-det-R (5'-GTTGCTGT-CACGCTCCC-3'; SEQ ID NO: 4). In an embodiment, the valN-inactivated mutant strain has antifungal activity and the ValN nucleic acid sequence within the validamycin gene cluster has a nucleic acid sequence with at least 95% sequence identity to SEQ ID NO: 5. In a particular embodiment, the nucleic acid sequence is as set forth in SEQ ID NO: 5.

In some embodiments, the resulting mutant strain is then cultured under conditions sufficient to allow the production of validamycin analogs, such as 1,1'-bis-valienamine and validienamycin. By way of example, the mutant strain is cultured at 37° C. in yeast extract, malt extract, and glucose (YMG) for 7 days. The produced validamycin analogs can then be isolated from the fermentation broth, according to techniques known to those of ordinary skill in the art. In one example, precipitation by solvent extraction from culture filtrate, which may use an adjusted to acid pH values and methods based on the anionic nature of the metabolite such as the use of anion exchange resins can be utilized. Other primary methods of isolation which may be used include conventional methods such as adsorption onto carbon, precipitation, salting out, molecular filtration, or any method known in the art. In one specific example, validamycin analogs, including 1,1'-bis-valienamine and validienamycin, can be isolated from fermentation broth through a two-column chromatography system. For example, the two-column chromatography system can include Dowex 50W×8 ($H^+$ form) and Dowex 1×8 ($OH^-$ form).

In some embodiments, the method further includes converting 1,1'-bis-valienamine to valienamine, such as by treating the 1,1'-bis-valienamine with N-bromosuccinimide (NBS). The method can also include purifying the resulting product following treatment of 1,1'-bis-valienamine with NBS, such as by methods known to one of ordinary skill in the art (including ion exchange column chromatography), to produce substantially pure valienamine. In even further embodiments, the method includes converting the substantially pure valienamine to the antidiabetic drug, voglibose. Thus, this method can be used to provide an alternative avenue to this precursor of antidiabetic drugs.

IV. Validamycin Analogs

Also disclosed herein are validamycin analogs with the following chemical structures:

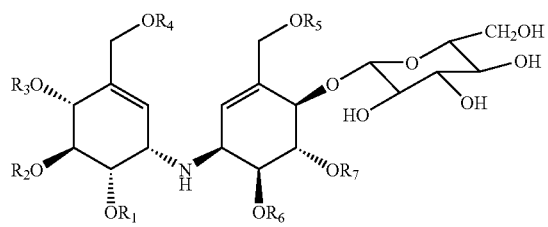

wherein $R_1$-$R_7$ independently are selected from H, acyl, carbohydrate, lower alkyl, amino acid, fatty acid, and protecting groups. In particular examples, the validamycin analog has the chemical structure of

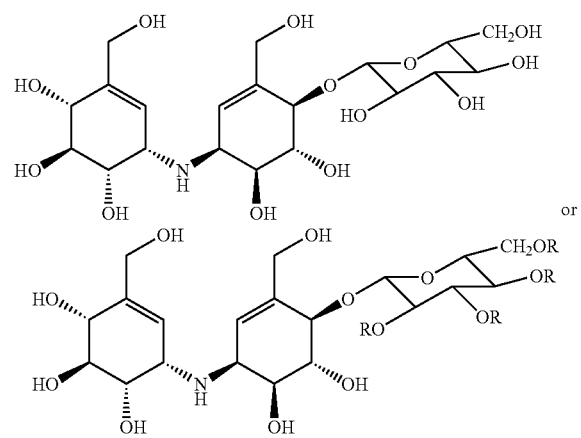

wherein R is an acetyl or benzyl group.

In some embodiments, a validamycin analog has the chemical structure of

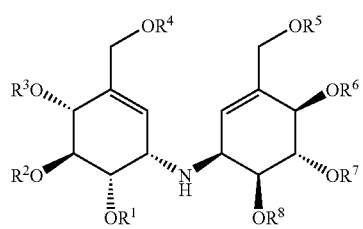

wherein $R^1$-$R^8$ independently are selected from H, acyl, carbohydrate, lower alkyl, amino acid, fatty acid, and protecting groups. In one example, the compound has the formula

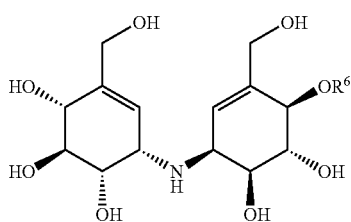

wherein $R^6$ is selected from acyl, lower alkyl, carbohydrate, amino acid, or protecting groups. In one specific example, $R^6$ is a carbohydrate, such as a hexose.

V. Compositions

The present disclosure also relates to compositions comprising a biological agent as described herein. The biological agent may be a compound, such as 1,1'-bis-valienamine, a 1,1'-bis-valienamine derivative, validienamycin, or a validienamycin derivative obtained from a mutant validamycin A strain, or a combination thereof, having the biological activity of interest. The composition can include a suitable carrier. Optionally, the agent is affixed to a substrate or surface. The compositions including a biologically active agent of the present disclosure can be used to inhibit a range of pathogenic organisms (such as fungi), diseases or conditions. The composition can also find use as applied to a substrate. The agent is provided in an amount effective to inhibit the pathogenic organism or condition for a time and under conditions permitting the agent to inhibit the pathogenic organism or condition. Different compositions will be required depending upon the mode of administration to plants.

Common carriers and excipients include, but are not limited to, corn starch, gelatin, lactose, sucrose, microcrystalline cellulose, kaolin, mannitol, dicalcium phosphate, sodium chloride, and alginic acid.

The disclosed validamycin analogs, or a salt or ester thereof, can be formulated into a pharmaceutical composition, which comprises the compound, together with a pharmaceutically acceptable carrier.

The compound may be in the form produced by the validamycin A mutant strain (e.g., a valN-inactivated mutant strain), or the result of further chemical modification, for instance to reduce toxicity and perhaps to increase efficacy or availability (e.g., availability in a biological system).

VI. Pesticidal Compositions

The compositions of the disclosure may be pesticidal (e.g., fungicidal) compositions used for administration to plants, or the associated soil, equipment, containers, machinery, surfaces and so forth. For use with a plant, the method of use may involve applying a product of a mutant strain of Streptomyces, such as a mutant strain of S. hygroscopicus in which valN is inactivated, or an extract or compound derived from the strain either directly to the plant, or to soil adjacent to the plant. In some cases the treatment may be made to seeds, e.g., in the format of seed coats, soaks, or other such applications. In certain circumstances, the strain (rather than the isolated composition or extract) can be applied to grow in association with the plant and produce biologically active compounds capable of protecting the plant against plant pathogen attack, such as fungal attack.

The present disclosure is further directed to pesticidal compositions comprising the active substance in an effective amount to control a pest, and a pesticidal carrier. For example, an effective amount is the amount of the substance sufficient to control a pest through killing or stunting of the growth of the pest or protecting a plant from pest infestation. The pesticidal compositions may comprise a compound of the present disclosure in a substantially pure form or as an extract from a whole broth culture of a mutant strain of Streptomyces, such as a mutant strain of S. hygroscopicus in which valN is inactivated, in dry, concentrated, or liquid form and a suitable pesticidal carrier, examples of which are disclosed infra. The substance is present in the composition at a concentration of about 0.001% to about 60% (w/w).

The pesticidal compositions may further comprise a deposition agent which assists in preventing the composition from drifting from the target area during application (e.g., as it is sprayed from a plane), or from being blown away from the plant once it has been deposited. The deposition agent in the compositions of the present disclosure is preferably a proteinaceous material, which has the added benefit of being palatable to the insect. Any animal or vegetable protein is suitable for this purpose, in dry or in liquid form. Examples of useful sources of protein which can be conveniently and economically added to the composition include, but are not limited to, soy protein, potato protein, soy flour, potato flour, fish meal, bone meal, yeast extract, and blood meal. Alternative deposition agents include modified cellulose (carboxymethylcellulose), botanicals (grain flours, ground plant parts), non-phyllosilites (talc, vermiculite, diatomaceous earth), natural clays (attapulgite, bentonite, kaolinite, montmorillonite), and synthetic clays (Laponite). When utilized, the deposition agent is present in the pesticidal compositions of the present disclosure in an amount of between about 0.4% w/w and about 50% w/w, preferably between about 1% w/w and about 20% w/w.

The pesticidal compositions may further comprise an antifreeze/humectant agent which suppresses the freeze point of the product and helps minimize evaporation when sprayed and which maintains deposit texture making the product more efficacious and palatable. Examples of antifreeze/humectant agents include, but are not limited to, ethylene glycol, propylene glycol, dipropylene glycol, glycerol, butylene glycols, pentylene glycols and hexylene glycols. When utilized, the antifreeze/humectant agent is present in the pesticidal compositions of the present disclosure in an amount of between about 0.5% w/w and about 25% w/w, preferably between about 2% w/w and about 15% w/w.

The pesticidal compositions may further comprise a surfactant in an amount where it acts as an emulsifying, a wetting, or a dispersing agent. Examples of such surfactants are anionic surfactants such as carboxylates, for example, a metal carboxylate of a long chain fatty acid; N-acylsarcosinates; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl naphthalene sulphonate; salts or sulphonated naphthalene-formaldehyde condensates; salts of sulphonated phenol-formaldehyde condensates; or more complex sulphonates such as amide sulphonates, e.g., the sulphonated condensation product of oleic acid and N-methyl taurine or the dialkyl sulphosuccinates, e.g., the sodium sulphonate or dioctyl succinate. Further examples of such surfactants are non-ionic surfactants such as condensation products of fatty acid esters, fatty alcohols, fatty acid amides or fatty-alkyl- or alkenyl-substituted phenols with ethylene oxide, block copolymers of ethylene oxide and propylene oxide, acetylenic glycols such as 2,4,7,9-tetraethyl-5-decyn-4,7-diol, or ethoxylated acetylenic glycols. Further examples of such surfactants are cationic surfactants such as aliphatic mono-, di-, or polyamine as acetates, naphthenates or oleates; oxygen-containing amines such as an amine oxide of polyoxyethylene alkylamine; amide-linked amines prepared by the condensation of a carboxylic acid with a di- or polyamine; or quaternary ammonium salts. When utilized, the surfactant is present in an amount of between about 0.5% w/w and about 25% w/w, preferably between about 1% w/w and about 8% w/w.

The pesticidal compositions may further comprise an inert material. Examples of inert materials include inorganic minerals such as diatomaceous earth, kaolin, mica, gypsum, fertilizer, phyllosilicates, carbonates, sulfates, or phosphates; organic materials such as sugars, starches, or cyclodextrins; or botanical materials such as wood products, cork, powdered corncobs, rice hulls, peanut hulls, and walnut shells.

The pesticidal compositions may further comprise a preservative, a feeding stimulant, an attractant, an encapsulating pesticide, a binder, a dye, an ultraviolet light protectant, a buffer, a flow agent, or other component to facilitate product handling and application for particular target pests.

The pesticidal compositions can be applied in a dry or liquid form, e.g., a suspension, a solution, an emulsion, a dusting powder, a dispersible granule, a wettable powder, an emulsifiable concentrate, an aerosol or impregnated granule, or a concentrate or primary composition which requires dilution with a suitable quantity of water or other diluent before application. The concentrations of each component in the composition will vary depending upon the nature of the particular composition, specifically, whether it is a concentrate or to be used directly.

VII. Uses of the Disclosed Validamycin a Analogs to Control Fungal Infections

The present disclosure contemplates uses of the disclosed validamycin A analogs to control fungal infections, such as fungal infections of rice plants caused by *Rhizoctonia solani*.

The biologically active compounds of the present disclosure can be used to control a fungal pest or pathogen. The agent, including one of the disclosed compounds, is provided in an amount effective to inhibit the pathogenic organism for a time and under conditions permitting the agent to inhibit the pathogenic organism.

The disclosed validamycin A analogs, including validienamycin, have significant antifungal activity. In an example, the validamycin A analogs can be used to inhibit fungal infections. The disclosed analogs can be used to control diverse fungal pathogens including, but not limited to, *Rhizoctonia solani*, *Botrytis cinerea*, and *Sclerotinia sclerotiorum*. For example, a biologically active agent including one or more of the disclosed validamycin A analogs, such as validienamycin, 1,1'-bis-Valienamine, or a combination of such compounds, is employed to control fungi including *Rhizoctonia solani*, *Botrytis cinerea*, and *Sclerotinia sclerotiorum*. For example, the disclosed compounds can be used to treat or protect plants challenged or infected by any myriad of plant pathogens, such as pathogenic fungi, and may be used to treat diseases in the field, soil or in post harvest applications. Additional agricultural applications include, but are not limited to, treatment in seed coats, on agricultural implements, leaf or other plant surfaces, and building or other material surfaces—generally, any site which may contain or come into contact with a pest or pathogen, such as a fungal pathogen or pest.

Treatment of Fungal Infections

The composition may contain about 1% to about 98% of a solid or liquid inert carrier. The compositions will be preferably administered at the labeled rate for commercial products, preferably about 0.01 pound to 5.0 pounds per acre when in dry form and at about 0.01 pint to 25 pints per acre when in liquid form.

The pesticidal compositions can be applied directly to a plant by, for example, spraying or dusting at the time when the pest has begun to appear on the plant or before the appearance of pests as a protective measure. The pesticidal compositions can be applied by foliar, furrow, broadcast granule, "lay-by", or soil drench application. The compositions can also be applied directly to ponds, lakes, streams, rivers, still water, and other areas subject to infestation by pests of concern to public health. The compositions can be applied by spraying, dusting, sprinkling, or other known methods to those of ordinary skill in the art. The spray or dust can conveniently contain another pesticide.

The pesticidal compositions can be applied to protect a number of different plant types, including, but not limited to, cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fiber plants (cotton, flax, hemp, jute), citrus fruit (oranges, lemons, grapefruit, mandarins), other fruits (such as bananas, pineapples, cassayas, mangos, guavas, grapes, and so forth), vegetables (spinach, lettuce, asparagus, cabbages and other brassicae, carrots, onions, tomatoes, potatoes), lauraceae (avocados, cinnamon, camphor), deciduous trees and conifers (linden-trees, yew-trees, oak-trees, alders, poplars, birch-trees, firs, larches, pines), or plants such as maize, turf plants, tobacco, nuts, coffee, sugar cane, tea, vines, hops, and natural rubber plants, as well as ornamental plants as well as ornamental plants and particularly plants which are grown for their flowers. It will be appreciated that the listed plants are representative only, rather than limiting.

The following examples are provided to illustrate certain particular features and/or embodiments. These examples should not be construed to limit the invention to the particular features or embodiments specifically described.

EXAMPLES

Example 1

Material and Methods

This example describes materials and methods utilized for the inactivation of valN, isolation of 1,1'-bis-valienamine and validienamycin, and characterization of these compounds.

Inactivation of valN by ReDirect Technology: The inactivation of valN in *Streptomyces hygroscopicus* subsp. *jinggangensis* 5008 was carried out using ReDirect Technology (Gust et al., *Proc. Natl. Acad. Sci. USA* 100: 1541-1546, 2003). A 1449-bp replacement fragment was obtained by amplifying the aac(3)IV-oriT cassette from pIJ773 using primers ValN-PCR-F (5'-GTGACTCTGGAGGAGGGCGGGCCCCGTCTGCAC CGCTCGATTCCGGGGATCCGTCGACC-3'; SEQ ID NO: 1) and ValN-PCR-R (5'-

TCAGAAGGGTTCGGGGTGGACAACGATCTTGCCGG GTCCTGTAGGCTGGAG CTGCTTC-3'; SEQ ID NO: 2) (homologous sequences for recombination are underlined). A 7096-bp BamHI fragment from cosmid 17F2 containing valN was cloned into BamHI digested pHZ1358, to generate pJTU751. Plasmid pJTU751 was then transferred into *E. coli* BW25113 harboring the λRED plasmid pIJ790. ValN in pJTU751 was replaced by the above PCR product to generate plasmid pJTU753, which has 3924-bp upstream and 2244-bp downstream sequences flanking the valN gene for double-crossover recombination and was transformed into *S. hygroscopicus* 5008 by conjugation. Replacement of valN in the resulting XH-2 mutant was confirmed by PCR amplification with the primers of ValN-det-F (5'-TGCTTCCGCTGCTTC-TAC-3'; SEQ ID NO: 3) and ValN-det-R (5'-GTTGCTGT-CACGCTCCC-3'; SEQ ID NO: 4).

Production and purification of 1,1'-bis-valienamine (3) and validienamycin (4): Mutant strain XH-2 was cultured at 37° C. in YMG (yeast extract, malt extract, and glucose) for 7 days. 1,1'-bis-Valienamine (20 mg) and validienamycin (8 mg) were isolated from fermentation broth (1 L) through a two-column chromatography system, using Dowex 50W×8 ($H^+$ form) (100 g) and Dowex 1×8 ($OH^-$ form) (80 g). The properties of isolated 1,1'-bis-Valienamine (3) were the following: $[\alpha]_D^{21}$+143.9 (c=0.2 in MeOH) {lit. (Shing et al., *J. Am. Chem. Soc.* 126: 15990-15992, 2004) $[\alpha]_D^{20}$+47.1 (c=1.0 in MeOH)}*; IR (thin film): n=3349, 2920, 1656, 1408, 1310, 1097, 1012 $cm^{-1}$. $^1$H NMR (300 MHz, $D_2O$, 23° C., DSS): δ=3.56 (dd, J=4.7, 4.8 Hz, 2H; H-1 and H-1'), 3.66 (dd, J=4.7, 10.0 Hz, 2H; H-2 and H-2'), 3.73 (dd, J=6.5, 10.0 Hz, 2H; H-3 and H-3'), 4.07 (d, J=6.5 Hz, 2H; H-4 and H-4'), 4.12 (d, J=13.9 Hz, 2H; H-7a and H-7'a), 4.24 (d, J=13.9 Hz, 2H; H-7b and H-7'b), 5.95 (brd, J=4.8 Hz, 2H; H-6 and H-6'). $^{13}$C NMR (75 MHz, $D_2O$, 23° C., DSS): δ=55.9 (C-1 and C-1'), 64.3 (C-7 and C-7'), 72.5 (C-2 and C-2'), 74.2 (C-4 and C-4'), 75.8 (C-3 and C-3'), 126.3 (C-6 and C-6'), 142.1 (C-5 and C-5'). ESI(+)-MS: m/z: 334.13 $[M+H]^+$; HRMS (ESI+): m/z: 356.1341 (calculated for $C_{14}H_{23}NO_8Na$: 356.1321). These studies were repeated three times in two different polarimeters. The $[\alpha]_D$ reading was consistently measured around +144 in all of the studies. Subsequently, 3 was converted to its peracetate derivative and its optical rotation was measured. The $[\alpha]_D$ value of the product was +107.3.

Biotransformation of 1,1'-bis-valienamine (3) to validienamycin (4): 1,1'-bis-Valienamine (4.2 mg, 0.013 mmol) was incubated with recombinant ValG (0.45 mg), $MgCl_2$ (1 mM), and UDP-glucose (10 mg, 0.018 mmol) in Tris-buffer (1.2 mL, 40 mM, pH 7.6) at 30° C. for 3 hours. Recombinant ValG was prepared according to the method reported previously (Bai et al., *Chem. Biol.* 13: 387-397, 2006). The reaction was quenched by addition of methanol (1.2 mL) and the mixture was centrifuged at 12,000 rpm for 10 minutes. The supernatant was transferred and the organic solvent was evaporated in vacuo. The aqueous solution was lyophilized and dissolved in water (0.5 mL). The solution was subjected to Dowex-50W×8 ($H^+$ form) and Dowex 1×8 ($OH^-$ form) columns to give pure validienamycin (5.6 mg, 0.011 mmol, 85% yield). Validienamycin (4) had the following properties: $[\alpha]_D^{21}$+124.6° (c=1.0 in MeOH); IR (thin film): ν=3353, 2918, 1653, 1419, 1075 $cm^{-1}$. $^1$H NMR (300 MHz, $D_2O$, 23° C., DSS): δ=3.33 (dd, J=8.0, 9.2 Hz, 1H; H-2"), 3.41 (dd, J=9.4, 9.2 Hz, 1H; H-4"), 3.50 (d, J=9.2 Hz, 1H; H-3"), 3.51 (m, 1H; H-5"), 3.55 (m, 2H; H-1', H-1), 3.67 (m, 1H; H-2), 3.69 (d, J=6.5 Hz, 1H; H-4), 3.74 (m, 1H; H-6"), 3.76 (dd, J=5.1, 9.5 Hz, 1H; H-2'), 3.94 (dd, J=2.0, 12.4 Hz, 1H; H-6"), 4.01 (dd, J=5.9, 9.5 Hz, 1H; H-3'), 4.07 (d, J=6.5 Hz, 1H; H-3), 4.14 (brt, J=13.9 Hz, 2H; H-7), 4.22 (m, 1H; H-4'), 4.27 (brt, J=14.1 Hz, 2H; H-7'), 4.64 (d, J=8.0 Hz, 1H; H-1"), 5.96 (brd, J=5.0 Hz, 1H; H-6), 6.02 (brd, J=4.6 Hz, 1H; H-6'). $^{13}$C NMR (75 MHz, $D_2O$, 23° C., DSS): δ=55.5 (C-1'), 55.9 (C-1'), 63.4 (C-6"), 64.3 (C-7), 64.5 (C-7'), 72.0 (C-2'), 72.3 (C-4"), 72.5 (C-2), 74.2 (C-3), 74.3 (C-3'), 75.9 (C-4), 76.1 (C-2"), 78.4 (C-5"), 78.7 (C-3"), 84.4 (C-4'), 106.3 (C-1"), 126.3 (C-6), 128.5 (C-6'), 140.0 (C-5'), 142.2 (C-5). ESI(+)-MS: m/z: 496.13 $[M+H]^+$; HRMS (ESI+): m/z: 518.1850 (calculated for $C_{20}H_{33}NO_{13}Na$: 518.1850).

Fungal growth inhibitory assay of 1,1'-bis-valienamine (3) and validienamycin (4): 1% agar (14 mL) was mixed with the compounds (dissolved in 1 mL $H_2O$) and then plated into Petri dishes. Discs of PDA agar with mycelia of *Pellicularia sasakii* were placed in the center of the above plates as the indicator strain for bioassay of the compounds. The plates were incubated at 30° C. for 2 days.

Cleavage of 1,1-bis-valienamine with NBS to produce valienamine. To a solution of 1,1'-bis-valienamine (13 mg, 0.039 mmol) in $DMF/H_2O$ (4:1, 0.4 mL), NBS (10.4 mg, 0.0585 mmol) was added and the reaction mixture was stirred for 12 hours at room temperature. The reaction mixture was diluted with $H_2O$ (5 mL) and $CH_2Cl_2$ (5 mL) and the aqueous layer was collected and lyophilized. The crude residue was redissolved in $H_2O$ (1 mL) and subjected to Dowex 50W×2 ($H^+$ form) column chromatography. The column was washed with $H_2O$ (75 mL) and the compounds were eluted with 0.5 M $NH_4OH$ solution (75 mL) and lyophilized. The residue was then subjected to a Dowex 1×8 ($OH^-$ form) column and eluted with $H_2O$ to give valienamine and a trace amount of the starting material. The pure product was then obtained by silica gel column chromatography ($CHCl_3$:MeOH:aq. 5% $NH_4OH$ (15 M)=3:6:1). $^1$H NMR (300 MHz, $D_2O$): $δ_{DSS}$=3.54 (m, 1H; H-1), 3.72 (m, 2H; H-2, H-3), 4.13 (m, 1H; H-4), 4.15 (d, J=13.6, 1H; H-7a), 4.27 (d, J=13.5, 1H; H-7b), 5.84 (m, 1H; H-6).

Cleavage of validoxylamine A (2) with NBS to produce valienamine and validamine. To a solution of validoxylamine A (2) (20 mg, 0.060 mmol) in $DMF/H_2O$ (4:1, 0.5 mL) NBS (15.9 mg, 0.0895 mmol) was added and the reaction mixture was stirred for 8 hours at room temperature. The reaction mixture was diluted with $H_2O$ (5 mL) and $CH_2Cl_2$ (5 mL) and the aqueous layer was collected and lyophilized. The residue was dissolved in $H_2O$ (1 mL) and subjected to Dowex 50W×2 ($H^+$ form) column chromatography. The column was washed with $H_2O$ (100 mL) and the compounds were eluted with 0.5 M $NH_4OH$ solution (100 mL) and lyophilized. The residue was chromatographed on Dowex 1×8 ($OH^-$ form) with $H_2O$ as eluent to give a 1:1 mixture of valienamine and validamine (based on $^1$H-NMR integration).

Example 2

This example describes the production of a valN-inactivated mutant, XH-2.

Figure 1:
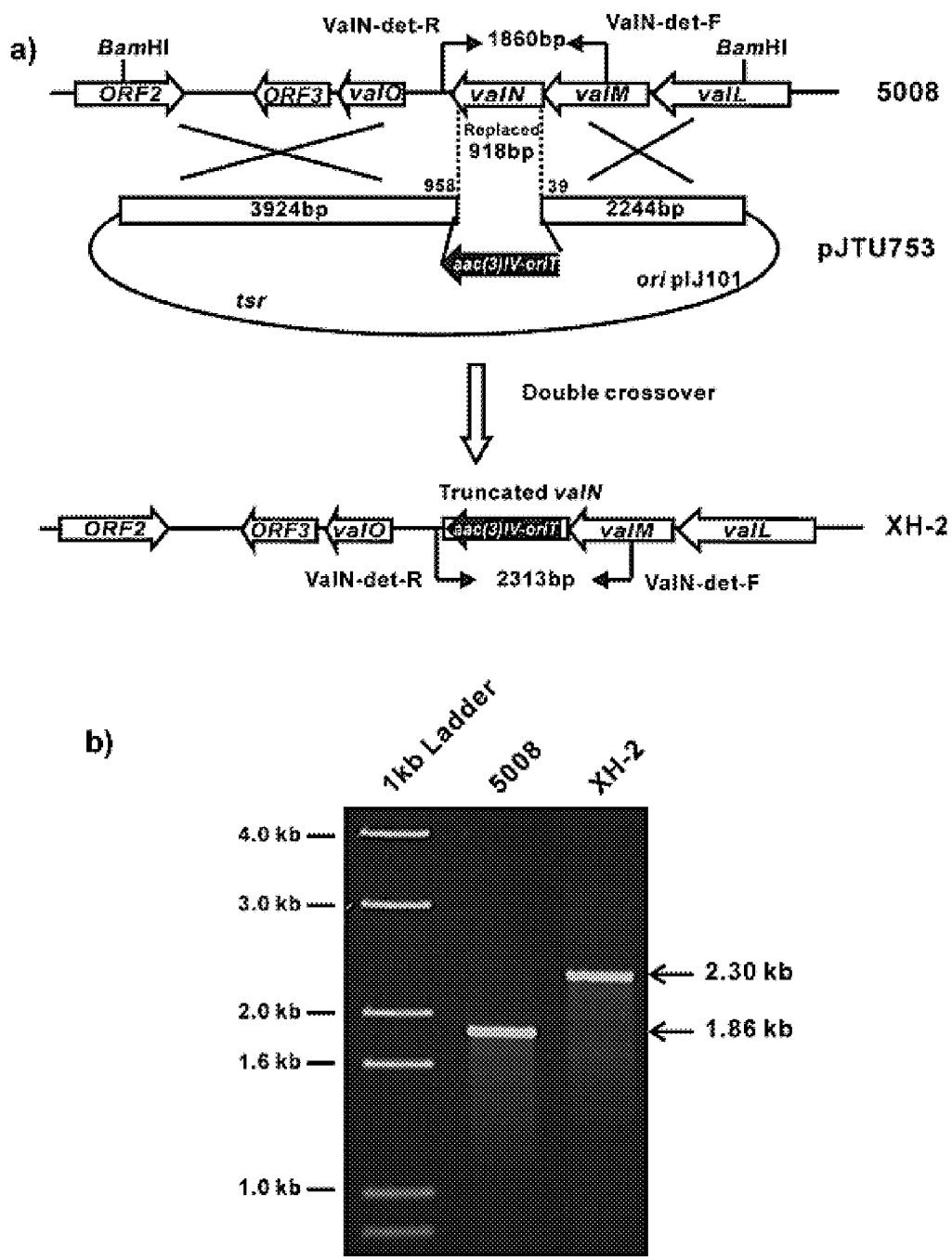
FIG. 1 illustrates the inactivation of valN in *S. hygroscopicus* 5008. Panel A is a schematic representation of the replacement of a 918-bp fragment of valN with the 1371-bp aac(3) IV-oriT cassette, wherein shuttle plasmid pJTU753, aac(3) IV-oriT was inserted between the 3924-bp and 2244-bp genomic fragments originally flanking the 918-bp region. Panel B is a digital image of an agarose gel illustrating PCR analysis of wild-type 5008 and mutant XH-2 amplicons. Wild-type 5008 produced a 1860-bp PCR-amplified product and mutant XH-2 yielded a 2313-bp product using primers ValN-det-F (SEQ ID NO: 3) and ValN-det-R (SEQ ID NO: 4).

To inactivate valN in *S. hygroscopicus* 5008, the gene in the genome was replaced by an aac(3)IV-oriT cassette (FIG. 1A) (Gust et al., *Proc. Natl. Acad. Sci. USA* 100: 1541-1546, 2003). A pHZ1358-derived plasmid (pJTU753) which contained an aac(3)IV-oriT cassette flanked with sequences of 3924-bp upstream and 2244-bp downstream of valN was obtained by ReDirect Technology in *E. coli* BW25113 (pIJ790) (Gust et al., *Proc. Natl. Acad. Sci. USA* 100: 1541-1546, 2003). The plasmid pJTU753 was introduced into strain 5008 by conjugation from *E. coli* ET12567 (pUZ8002) and the apramycin-resistant phenotype was screened to get the valN-inactivated mutant, XH-2. Total DNA was extracted from mutant (XH-2) and wild-type S. hygroscopicus 5008 as template for PCR amplification using as primers SEQ ID NOs: 3 and 4. The mutant gave a 2.30-kb PCR product and the wild-type gave a 1.86-kb PCR product (FIG. 1B), which confirmed that a 918-bp DNA fragment of valN has been replaced by the 1371-bp aac(3)IV-oriT cassette. These studies illustrate a method that can be employed to produce a mutant strain of S. hygroscopicus in which valN is inactivated.

Example 3

This example describes the isolation and structure elucidation of 1,1'-bis-valienamine and validienamycin.

Mutant strain XH-2 was cultured at 37° C. in YMG medium for 7 days and the culture broth was directly analyzed by TLC and LC-MS. Neither validamycin A (1) (MW=497) nor validoxylamine A (2) (MW=335) were found in the culture broth of XH-2, confirming the involvement of ValN in 1 biosynthesis. However, two new peaks were observed in the mass spectra at m/z 496 and 334. As ValN was originally thought to be a dehydrogenase that was responsible for the reduction of the C-1 keto group of valienone 7-phosphate to 1-epi-valienol 7-phosphate (Bai et al., Chem. Biol. 13: 387-397, 2006; Zhang et al., J. Biol. Chem. 277: 22853-22862, 2002), the production of the two new metabolites by the XH-2 mutant was rather unexpected. Therefore, a 2.5 L culture of XH-2 was fermented for 7 days and the culture broth was subjected to Dowex 50W×8 ($H^+$ form) and Dowex 1×8 ($OH^-$ form) column chromatography. Guided by thin layer chromatography (TLC) and mass spectrometry (MS) analyses, the two compounds (20 mg/L of that with m/z 334 and 8 mg/L of that with m/z 496) were isolated.

Figure 3:
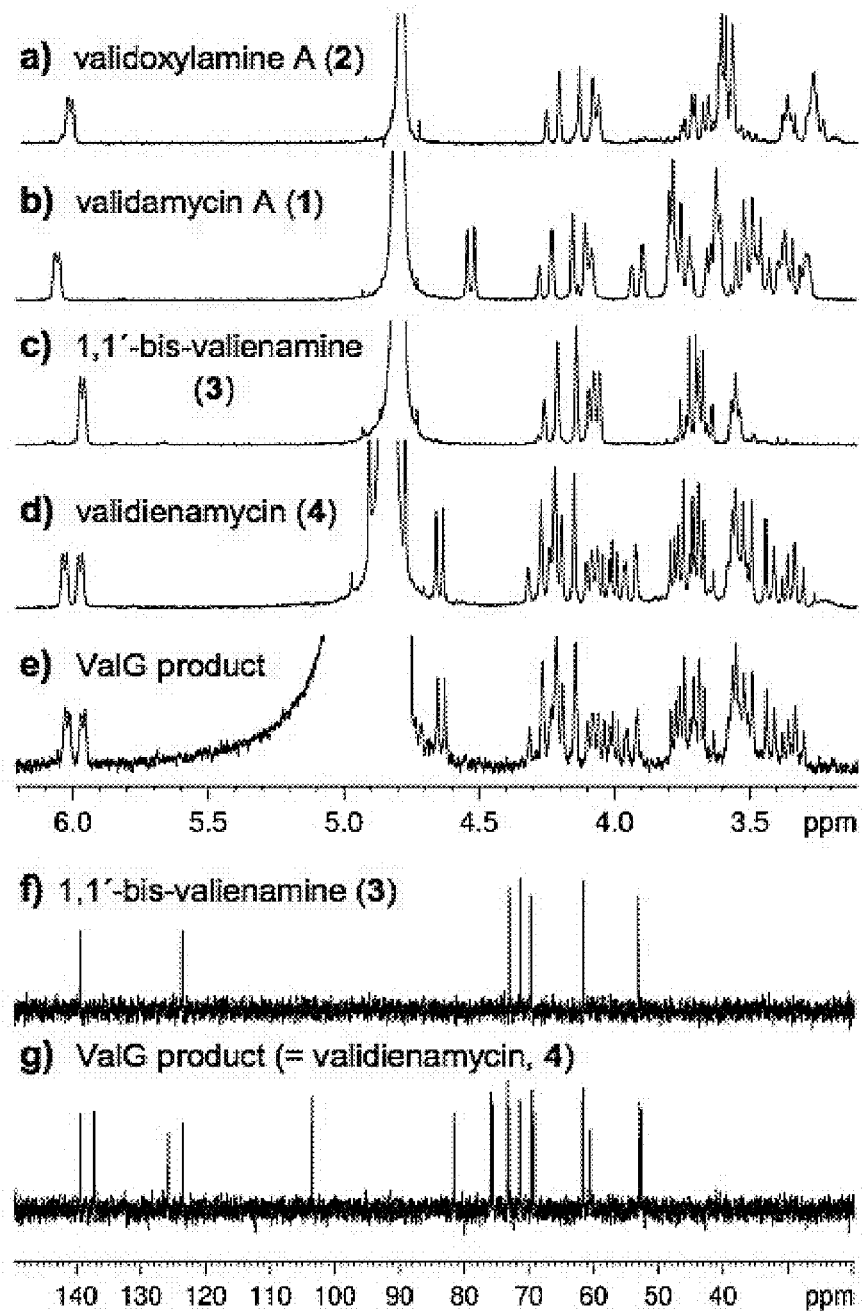
FIG. 3 provides a series of $^1$H- and $^{13}$C Nuclear Magnetic Resonance (NMR) spectra of validamycin analogs including $^1$H NMR spectrum of validoxylamine A (Panel A), $^1$H NMR spectrum of validamycin A (Panel B), $^1$H NMR spectrum of 1,1'-bis-valienamine (Panel C), $^1$H NMR spectrum of validienamycin (Panel D), $^1$H NMR spectrum of ValG Product (Panel E), $^{13}$C NMR spectrum of 1,1'-bis-valienamine (Panel F), and $^{13}$C NMR spectrum of validienamycin (Panel G).

The chemical structure of the major metabolite was first elucidated on the basis of its 1D- and 2D NMR and MS data. In spite of having a molecular mass of 333, which is only two atomic mass units less than that of 2, the compound showed much simpler $^1H$- and $^{13}C$ NMR spectra (FIG. 3). Only seven carbon signals were observed in its $^{13}C$ NMR spectrum (FIG. 3F). The presence of an olefinic proton signal at 5.95 ppm (brd, J=4.8 Hz) typical for an unsaturated cyclitol moiety suggested that it contains a valienamine moiety. Taking into account the molecular mass of the compound, it was proposed that the compound is a symmetrical dimer of valienamine (1,1'-bis-valienamine, 3).

Example 4

This example describes a method of glycosylation of 1,1'-bis-valienamine.

To confirm the chemical structure of 1,1'-bis-valienamine, the compound was then subjected to an enzymatic desymmetrization by converting it to its glycosylated product using the glycosyltransferase ValG in the presence of $Mg^{2+}$ and UDP-glucose. The product was purified using ion-exchange column chromatography and analyzed by NMR and MS. The $^1H$ NMR spectrum of the product revealed the presence of two olefinic protons [5.96 (brd, J=5.0 Hz), 6.02 (brd, J=4.6 Hz)] and an anomeric proton [4.64 (d, J=8.0 Hz)], in addition to other protons designated to the core aminocyclitol and glucose (FIG. 3E). The $^{13}C$ NMR spectrum showed twenty carbon signals (FIG. 3G). Among them are four olefinic carbon signals [126.3 (C-6), 128.5 (C-6'), 140.0 (C-5'), 142.2 (C-5)] and an anomeric carbon [106.3 (C-1")], confirming the nature of the product as a pseudotrisaccharide, which consists of two valienamine moieties—coupled to each other via a nitrogen bridge—and glucose. This proposed structure was consistent with the ms data (m/z 496 [M+H]$^+$). Two-dimensional NMR analysis confirmed the glucose attachment at the C-4' position, which is consistent with the regioselectivity of ValG (Bai et al., Chem. Biol. 13: 387-397, 2006). The enzyme product is identical with the second metabolite isolated from the mutant, which was identified as a new compound, validienamycin (4).

Example 5

This example demonstrates the antifungal activity of 1,1'-bis-valienamine and validienamycin.

Figure 4:
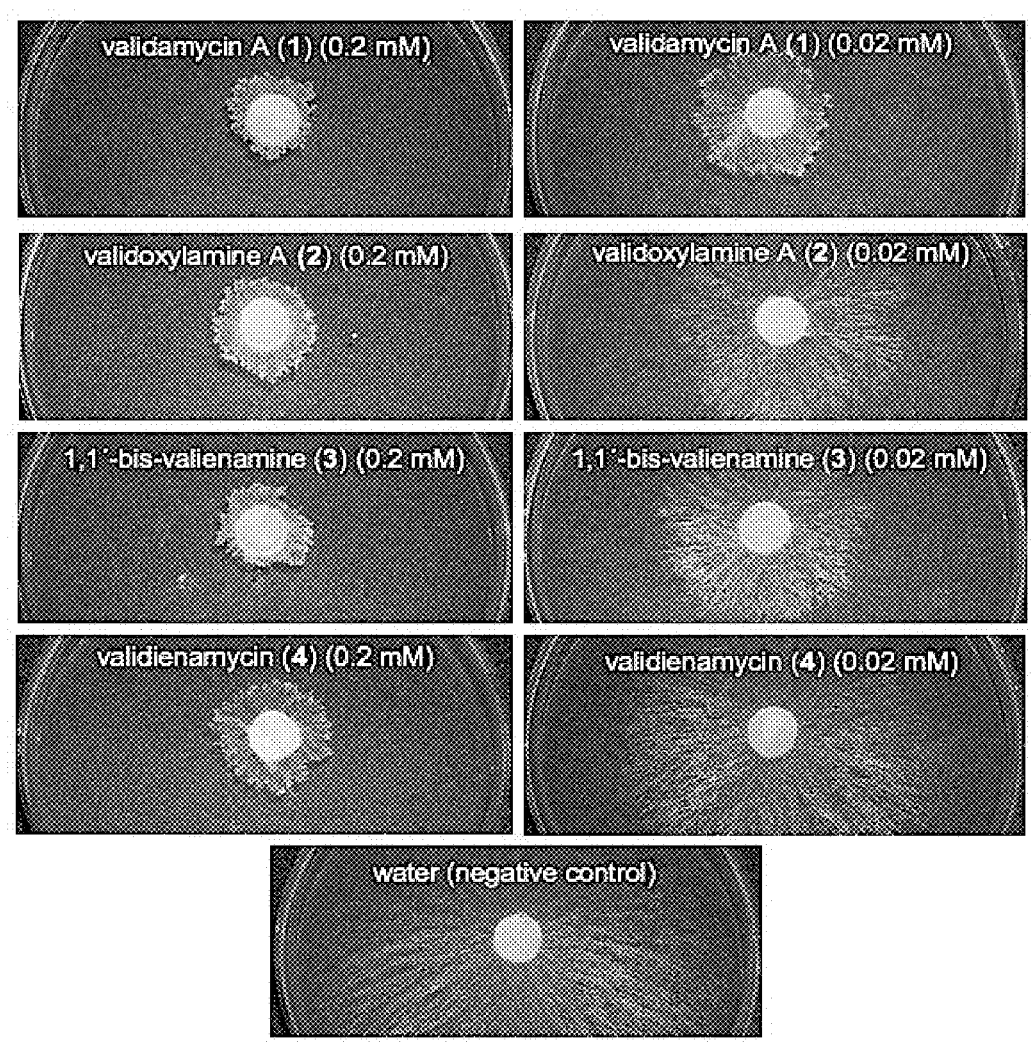
FIG. 4 provides a series of digital images illustrating the antifungal activity of the indicated validamycin A analogs.
Figure 5:
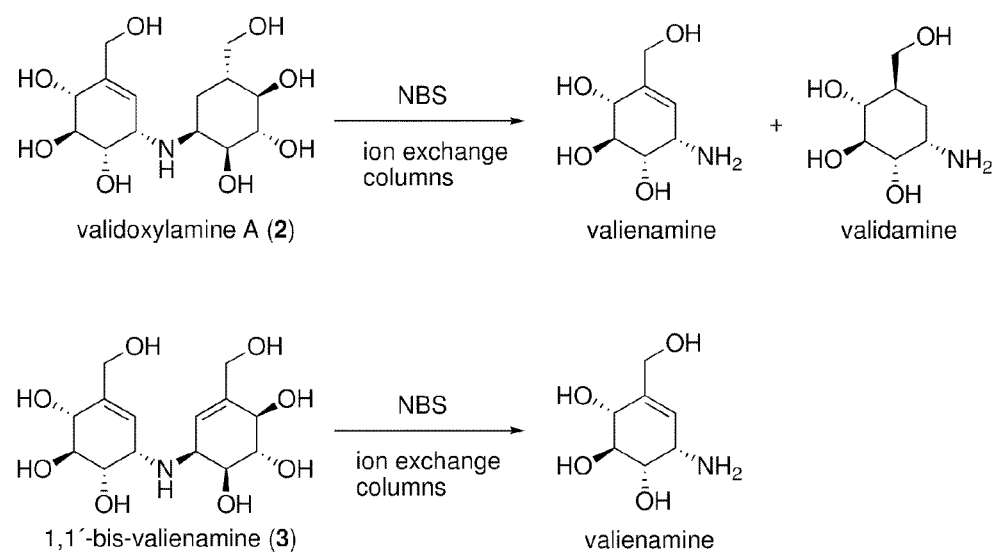
FIG. 5 provides chemical degradation pathways of validoxylamine A and 1,1'-bis-valienamine.

Antifungal activity assays of compounds 3 and 4 were tested against Pellicularia sasakii (=R. solani) using an agar plug assay (Minagawa et al., Chembiochem 8: 632-641, 2007). Agar plugs with diameter of 5 mm and containing P. sasakii mycelia were placed in the center of agar plates that contain each compound and the growth of the pathogen was monitored after two days. Active compounds were determined based on their ability to inhibit the expansion of the fungal mycelia on the Petri dishes. The results revealed that at 0.2 mM concentration, 3 and 4 demonstrated a comparable fungistatic activity with 1 and 2. However, at a lower concentration (0.02 mM), 1 is the most active compound among those evaluated (FIG. 4).

Example 6

This example describes the conversion of 1,1'-bis-valienamine and validienamycin to valienamine.

Taking advantage of the ability to produce 1,1'-bis-valienamine and validienamycin by fermentation as illustrated in the prior examples, an efficient methodology was developed for the production and purification of valienamine. 1,1'-bis-Valienamine contains two identical unsaturated cyclitol units and its efficient conversion to valienamine can provide an alternative avenue to this precursor of antidiabetic drugs. The glucoside validienamycin can be hydrolyzed to 1,1'-bis-valienamine by refluxing the compound in 1N $H_2SO_4$/AcOH (1:1) for 48 hours. Such procedure has previously been reported for validamycin A to give validoxylamine A, which can be subsequently cleaved by using N-bromosuccinimide (NBS) to give the corresponding aminocyclitols and ketones (Ogawa et al., Chem. Lett. 18: 725-728, 1989; Ogawa et al., J. Chem. Soc. Perkin Trans. I: 3287-3290, 1991).

A similar procedure was also used for the chemical cleavage of 1,1'-bis-valienamine. However, in contrast to the cleavage of validoxylamine A that gave multiple products, treatment of 1,1'-bis-valienamine with N-bromosuccinimide (NBS) was hypothesized to give only valienamine and its corresponding ketone, which can be easily separated by ion exchange column chromatography.

Figure 6:
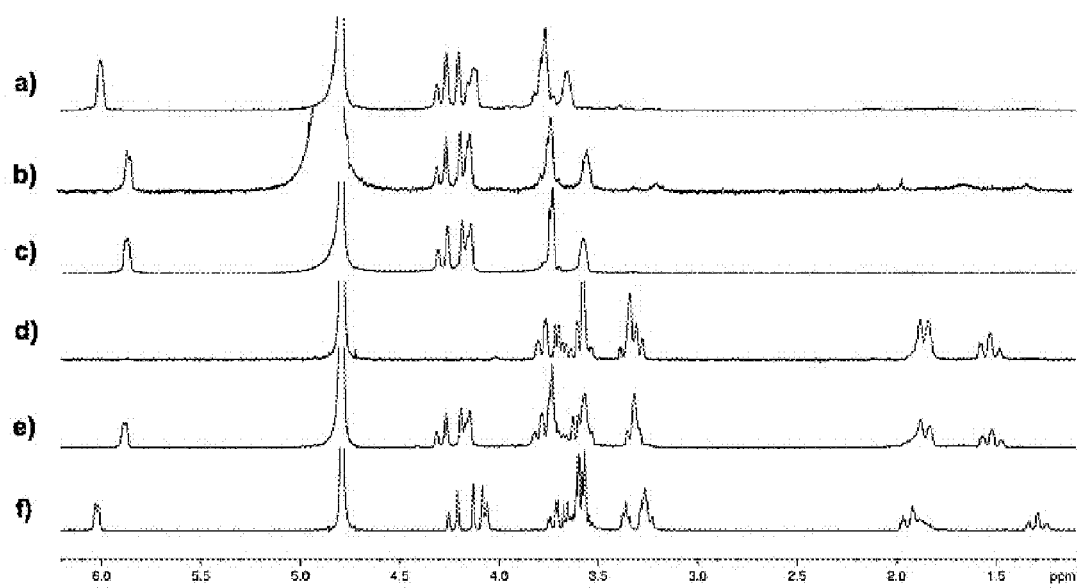
FIG. 6 provides a series of $^1$H NMR spectra including $^1$H NMR spectra of 1,1'-bis-valienamine (Panel A), degradation products of 1,1'-bis-valienamine treated with NBS and purified by ion exchange and silica gel columns (Panel B), valienamine standard (Panel C); validamine standard (Panel D); degradation products of validoxylamine A treated with NBS and purified by ion exchange columns (Panel E), and validoxylamine A (Panel F).

As shown in FIG. 6, cleavage of validoxylamine A with NBS and purification with Dowex 50W×8 ($H^+$ form) and Dowex 1×8 ($OH^-$ form) columns gave an approximately 1:1 mixture of valienamine and validamine, whereas similar treatments of 1,1'-bis-valienamine gave only valienamine as a product with a trace amount of unreacted starting material, which was removed by silica gel column chromatography to give pure valienamine (FIG. 6B).

These studies demonstrate an efficient method for the conversion of 1,1'-bis-valienamine and validienamycin to valienamine. The disclosed method can be used to provide an alternative avenue to this precursor of antidiabetic drugs.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound of the formula

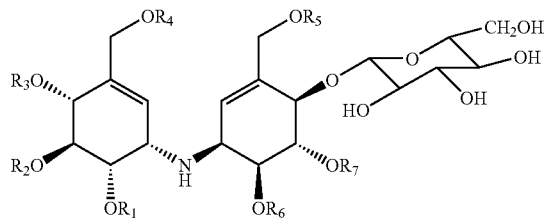

wherein $R_1$-$R_7$ independently are selected from H, acyl, carbohydrate, lower alkyl, amino acid, fatty acid, and protecting groups.

2. The compound according to claim 1, having the structure

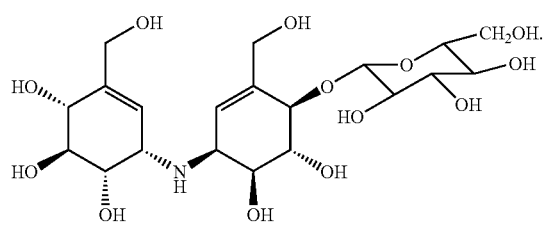

3. A compound of the formula

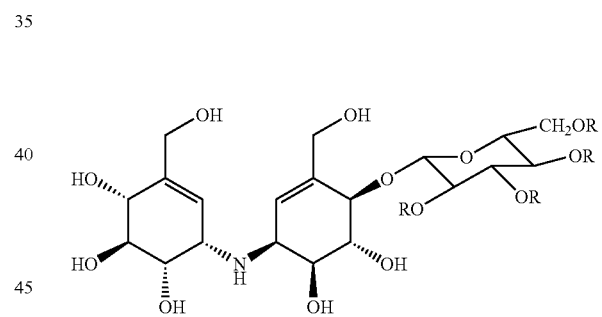

wherein R is an acetyl or benzyl group.

* * * * *

SEQUENCE LISTING

<160> NUMBER OF SEQ ID NOS: 5

<210> SEQ ID NO 1
<211> LENGTH: 59
<212> TYPE: DNA
<213> ORGANISM: Artificial Sequence
<220> FEATURE:
<223> OTHER INFORMATION: synthetic oligonucleotide primer for valN

<400> SEQUENCE: 1
gtgactctgg aggagggcgg gccccgtctg caccgctcga ttccggggat ccgtcgacc        59

<210> SEQ ID NO 2
<211> LENGTH: 58
<212> TYPE: DNA
<213> ORGANISM: Artificial Sequence
<220> FEATURE:
<223> OTHER INFORMATION: synthetic oligonucleotide primer for valN

<400> SEQUENCE: 2
tcagaagggt tcggggtgga caacgatctt gccgggtcct gtaggctgga gctgcttc         58

<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide primer for valN

<400> SEQUENCE: 3
tgcttccgct gcttctac                                                     18

<210> SEQ ID NO 4
<211> LENGTH: 17
<212> TYPE: DNA
<213> ORGANISM: Artificial Sequence
<220> FEATURE:
<223> OTHER INFORMATION: synthetic oligonucleotide primer for valN

<400> SEQUENCE: 4
gttgctgtca cgctccc                                                      17

<210> SEQ ID NO 5
<211> LENGTH: 1449
<212> TYPE: DNA
<213> ORGANISM: Artificial Sequence
<220> FEATURE:
<223> OTHER INFORMATION: DNA sequence of mutant valN

<400> SEQUENCE: 5
gtgactctgg aggagggcgg gccccgtctg caccgctcga ttccggggat ccgtcgacct        60
gcagttcgaa gttcctattc tctagaaagt ataggaactt cgaagttccc gccagcctcg      120
cagagcagga ttcccgttga gcaccgccag gtgcgaataa gggacagtga agaaggaaca      180
cccgctcgcg ggtgggccta cttcacctat cctgcccggc tgacgccgtt ggatacacca      240
aggaaagtct acacgaaccc tttggcaaaa tcctgtatat cgtgcgaaaa aggatggata      300
taccgaaaaa atcgctataa tgaccccgaa gcagggttat gcagcggaaa atgcagctca      360
cggtaactga tgccgtatttt gcagtaccag cgtacggccc acagaatgat gtcacgctga    420
aaatgccggc ctttgaatgg gttcatgtgc agctccatca gcaaaagggg atgataagtt    480

```
tatcaccacc gactatttgc aacagtgccg ttgatcgtgc tatgatcgac tgatgtcatc    540
agcggtggag tgcaatgtcg tgcaatacga atggcgaaaa gccgagctca tcggtcagct    600
tctcaacctt ggggttaccc ccggcggtgt gctgctggtc cacagctcct tccgtagcgt    660
ccggcccctc gaagatgggc cacttggact gatcgaggcc ctgcgtgctg cgctgggtcc    720
gggagggacg ctcgtcatgc cctcgtggtc aggtctggac gacgagccgt tcgatcctgc    780
cacgtcgccc gttacaccgg accttggagt tgtctctgac acattctggc gcctgccaaa    840
tgtaaagcgc agcgcccatc catttgcctt tgcggcagcg gggccacagg cagagcagat    900
catctctgat ccattgcccc tgccacctca ctcgcctgca agcccggtcg cccgtgtcca    960
tgaactcgat gggcaggtac ttctcctcgg cgtgggacac gatgccaaca cgacgctgca   1020
tcttgccgag ttgatggcaa aggttcccta tggggtgccg agacactgca ccattcttca   1080
ggatggcaag ttggtacgcg tcgattatct cgagaatgac cactgctgtg agcgctttgc   1140
cttggcggac aggtggctca aggagaagag ccttcagaag gaaggtccag tcggtcatgc   1200
ctttgctcgg ttgatccgct cccgcgacat tgtggcgaca gccctgggtc aactgggccg   1260
agatccgttg atcttcctgc atccgccaga gggcgggatg cgaagaatgc gatgccgctc   1320
gccagtcgat tggctgagct catgaagttc ctattccgaa gttcctattc tctagaaagt   1380
ataggaactt cgaagcagct ccagcctaca ggacccggca agatcgttgt ccaccccgaa   1440
cccttctga                                                           1449
```